(12) United States Patent
Berg et al.

(10) Patent No.: US 9,549,964 B2
(45) Date of Patent: Jan. 24, 2017

(54) DIAGNOSIS, PROGNOSIS, AND TREATMENT OF KIDNEY DISEASE

(75) Inventors: Anders H. Berg, Dedham, MA (US); S. Ananth Karumanchi, Chestnut Hill, MA (US); Ravi I. Thadhani, Boston, MA (US)

(73) Assignees: Beth Israel Deaconess Medical Center, Inc., Boston, MA (US); The General Hospital Corporation, Boston, MA (US)

( * ) Notice: Subject to any disclaimer, the term of this patent is extended or adjusted under 35 U.S.C. 154(b) by 87 days.

(21) Appl. No.: 14/131,866

(22) PCT Filed: Jul. 13, 2012

(86) PCT No.: PCT/US2012/046684
§ 371 (c)(1),
(2), (4) Date: Apr. 29, 2014

(87) PCT Pub. No.: WO2013/010085
PCT Pub. Date: Jan. 17, 2013

(65) Prior Publication Data
US 2014/0228296 A1 Aug. 14, 2014

Related U.S. Application Data

(60) Provisional application No. 61/551,645, filed on Oct. 26, 2011, provisional application No. 61/507,298, filed on Jul. 13, 2011.

(51) Int. Cl.
| | |
|---|---|
| *A61K 31/198* | (2006.01) |
| *A61K 38/06* | (2006.01) |
| *A61K 38/05* | (2006.01) |
| *A61K 45/06* | (2006.01) |
| *G01N 33/68* | (2006.01) |
| *C07K 16/20* | (2006.01) |
| *A61K 31/145* | (2006.01) |
| *A61K 31/255* | (2006.01) |
| *A61K 31/4172* | (2006.01) |

(52) U.S. Cl.
CPC ........... *A61K 38/063* (2013.01); *A61K 31/145* (2013.01); *A61K 31/198* (2013.01); *A61K 31/255* (2013.01); *A61K 31/4172* (2013.01); *A61K 38/05* (2013.01); *A61K 38/06* (2013.01); *A61K 45/06* (2013.01); *C07K 16/205* (2013.01); *G01N 33/6806* (2013.01); *G01N 33/6893* (2013.01); *C07K 2317/33* (2013.01); *C07K 2317/34* (2013.01); *G01N 2333/765* (2013.01); *G01N 2440/00* (2013.01); *G01N 2800/347* (2013.01)

(58) Field of Classification Search
CPC .................................................... A61K 31/198
See application file for complete search history.

(56) References Cited

U.S. PATENT DOCUMENTS

2011/0104818 A1 5/2011 Hazen et al.

OTHER PUBLICATIONS

Apostolov et al. (Clinical Chemistry 51:4, 719-728, 2005).*
Balion et al., "Carbamylated hemoglobin and carbamylated plasma protein in hemodialyzed patients," Kidney Int. 53(2):488-95 (1998).
Coca et al., "Biomarkers for the diagnosis and risk stratification of acute kidney injury: a systematic review." Kidney Int. 73(9):1008-16 (2008).
International Search Report and Written Opinion for International Application No. PCT/US2012/046684, mailed Jan. 24, 2013 (10 pages).

* cited by examiner

*Primary Examiner* — Amber D Steele
(74) *Attorney, Agent, or Firm* — Clark & Elbing LLP; Kristina Bieker-Brady

(57) ABSTRACT

The present invention relates to the discovery that an increased fraction of albumin is carbamylated in patients suffering from kidney disease (e.g., end-stage renal disease) and that the fraction of carbamylated albumin is also correlated with increased disease severity, particularly risk of mortality. The present invention also relates to the discovery that free amino acids can reduce carbamylation of albumin. Based on these discoveries the present invention provides diagnostic and prognostic methods for patients suffering from, or suspected of suffering from kidney disease. The invention also provides methods for treating kidney disease by administration of a compound or composition that reduced protein carbamylation, such as free amino acids or dipeptides.

18 Claims, 14 Drawing Sheets

ALBU_HUMAN  Mass: 69321   Score: 33   Matches: 1(1) Sequences: 1
Query  Observed  Mr(expt)  Mr(calc)  Delta   Miss  Score  Expect  Rank  Unique  Peptide
1      678.90    1355.78   1355.78   -0.0030  0     35     0.031   1     U       E.RQIKKQTALVEL + Carbamyl (K)

Figure 3C

| Fragmentation products of m/z = +678.9 | | | | | | | |
|---|---|---|---|---|---|---|---|
| Expected m/z | | | | | | | Observed m/z |
| b-type | c-type | | | | y-type | z-type | |
| --- | --- | 1 | R | 11 | --- | --- | |
| 285.1670 | 302.1935 | 2 | Q | 10 | 1200.6947 | 1184.6759 | 285.2 |
| 398.2510 | 415.2776 | 3 | I | 9 | 1072.6361 | 1056.6174 | 398.4 |
| 526.3460 | 543.3725 | 4 | K | 8 | 959.5520 | 943.5333 | 526.3 |
| 697.4468 | 714.4733 | 5 | X | 7 | 831.4571 | 815.4383 | 697.5 |
| 825.5053 | 842.5319 | 6 | Q | 6 | 660.3563 | 644.3376 | 825.4 |
| 926.5530 | 943.5796 | 7 | T | 5 | 532.2977 | 516.2790 | 926.8 |
| 997.5901 | 1014.6167 | 8 | A | 4 | 431.2500 | 415.2313 | 997.5 |
| 1110.6742 | 1127.7008 | 9 | L | 3 | 360.2129 | 344.1942 | |
| 1209.7426 | 1226.7692 | 10 | V | 2 | 247.1288 | 231.1101 | 247.2 |
| --- | --- | 11 | E | 1 | 148.0604 | 132.0417 | |

Figure 3D

SEQUENCE LISTING

```
<160> NUMBER OF SEQ ID NOS: 1

<210> SEQ ID NO 1
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: x is lysine or N-e-carbamoyl-L-lysine

<400> SEQUENCE: 1

Arg Gln Ile Lys Xaa Gln Thr Ala Leu Val Glu
1               5                   10
```

DIAGNOSIS, PROGNOSIS, AND TREATMENT OF KIDNEY DISEASE

CROSS-REFERENCE TO RELATED APPLICATIONS

This application is the U.S. National Stage of PCT/US2012/046684 filed Jul. 13, 2012, which claims benefit of U.S. Provisional Application Nos. 61/507,298 filed Jul. 13, 2011, and 61/551,645 filed Oct. 26, 2011, all of which are hereby incorporated by reference.

BACKGROUND OF THE INVENTION

The invention relates to diagnostic, prognostic, and treatment methods for subjects suffering from kidney disease.

Chronic kidney disease (CKD) is estimated to affect 5-10% of adults in industrialized countries, such as the United States (Eknoyan et al., Kidney Int. 66:1310-4, 2004). Loss of renal function results in retention of excess water and metabolic wastes including urea. Intermittent hemodialysis (HD) is the mainstay of therapy for most patients with end-stage kidney disease (ESRD); however, mortality rates even after initiating HD remain distressingly high (de Jager et al., JAMA 302:1782-9, 2009). Attempts to optimize HD therapy by increasing patients' dose of dialysis have produced disappointing results in some instances (Eknoyan et al., N. Engl. J. Med. 347:2010-9, 2002), raising the question of whether effective clearance of soluble waste products is the only thing that these patients are lacking. Chronic uremia is associated with drastically increased cardiovascular risk (Lancet 2:1150-1, 1981). Individuals with CKD are 10-20 times likelier to die of cardiovascular causes than to survive long enough to require dialysis (Foley et al., Am. J. Kidney Dis. 32:S112-9, 1998). Proximate reasons for this association have been identified—accelerated atherosclerosis, hypertension, left ventricular hypertrophy—but the root causes linking CKD to cardiovascular disease (CVD) remain poorly understood (Lindner et al., N. Engl. J. Med. 290:697-701, 1974; Foley et al., Kidney Int. 47:186-92, 1995). Notably, the strongest and most validated pharmacologic means of modifying cardiovascular risk, cholesterol reduction with statins, does not appear to change outcomes in patients with ESRD (Wanner et al., N. Engl. J. Med. 353:238-48, 2005, Fellstrom et al., N. Engl. J. Med. 360:1395-407, 2009). This finding further suggests the existence of other mechanisms linking CKD to CVD (Karumanchi et al., Nat. Med. 16:38-40, 2010).

The clinical significance of chronically elevated urea concentrations in ESRD subjects remains controversial. Past studies have shown that average blood urea nitrogen (BUN) levels are not reliable predictors of mortality in CKD patients (Johnson et al., Mayo Clin. Proc. 47:21-9, 1972; Chertow et al., Kidney Int. 56:1872-8, 1999; Stosovic et al., Ren. Fail. 31:335-40, 2009), and although intermittent hemodialysis significantly reduces patients' average blood urea levels, the HEMO study found that increasing the dose of hemodialysis (as evidenced by increased equilibrated Kt/V) conferred no measurable survival benefit to these patients (Eknoyan et al., N. Engl. J. Med. 347:2010-9, 2002).

Thus, there is a need for improved diagnostic and prognostic methods for patients suffering from kidney disease, as well as methods for treating such patients.

SUMMARY OF THE INVENTION

The present invention is based on the discovery that the fraction of albumin that is carbamylated correlates with the presence of and mortality rates in kidney disease. Based on this discovery, the present invention features diagnostic methods, methods for reducing carbamylation and treating kidney disease, and antibodies capable of binding to carbamylated albumin.

Accordingly, in a first aspect, the invention features a method for diagnosing kidney disease (e.g., ESRD), determining the likelihood of developing kidney disease (e.g., ESRD), or determining the severity of kidney disease (e.g., ESRD) in a subject (e.g., a human). The method includes determining the fraction of carbamylated albumin (e.g., albumin carbamylated at lysine 549) in the subject, where an increased fraction of carbamylation of the albumin, as compared to a control, is indicative of the presence of kidney disease, an increased likelihood of developing kidney disease, or increased kidney disease severity. In certain embodiments, the disease severity is indicative of an increased risk of near-term mortality (e.g., within two years, one year, nine months, six months, three months, two months, or one month). The increased risk of mortality may determined based on the subject having greater than 0.60%, 0.65%, 0.70%, 0.75%, 0.85%, 0.90%, 0.95%, 1.00%, 1.05%, 1.10%, or 1.15% carbamylated albumin. In particular embodiments, the method includes determining the level of free amino acids in the subject, where a decreased level of free amino acids is indicative of increased disease severity.

In another aspect, the invention features a method that includes determining the fraction of carbamylated albumin (e.g., albumin carbamylated at lysine 549) in a subject (e.g., a human), where the subject has or is suspected of having kidney disease (e.g., ESRD).

In either of the above two aspects, the determining may be performed on a biological sample (e.g., a blood sample or a blood serum sample) taken from the subject. The determining may be performed using mass spectroscopy or using an antibody or an antigen-binding fragment thereof (e.g., an antibody that binds albumin carbamylated at lysine 549 but does not bind uncarbamylated albumin). The antibody or antibody fragment may be conjugated to a detectable label. In certain embodiments, the determining is performed using an enzyme-linked immunosorbent assay (ELISA).

In another aspect, the invention features a method of treating or treating prophylactically a subject (e.g., a human) having kidney disease (e.g., ESRD). The method includes administration of an effective amount of a composition capable of being carbamylated.

In a related aspect, the invention also features a method of reducing protein carbamylation in a subject (e.g., a human). The method includes administering to the subject an effective amount of a composition capable of being carbamylated. The subject may be suffering from kidney disease (e.g., ESRD).

In either of the above two aspects, the subject may be administered a free amino acid, a dipeptide, or a tripeptide (e.g., glycylglycine, cysteine and cysteamine, taurine, cysteamine, cysteine, histidine, arginine, glutathione, lysine, glycine, gluatmine, tryptophan, alanine, valine, proline, leucine, gluatmate, or a combination thereof). In particular embodiments, the subject is administered glycylglycine, cysteine and cysteamine, taurine, cysteamine, cysteine, histidine, arginine, glutathione, lysine, or a combination thereof. In one embodiment, the subject is administered glycylglycine. The composition may be administered by any route, including intravenous, oral, intraperitoneal, nasal, intramuscular, intradermal, intraarterial, intranasal, intravitreal, topical, peritoneal, subcutaneous, subconjunctival, intravesicularl, mucosal, intrapericardial, local, or by inhalation.

In another aspect, the invention features an antibody or antibody fragment that specifically binds albumin carbamylated at lysine 549, but does not bind uncarbamylated albumin. In certain embodiments, the antibody is detectably labeled (e.g., labeled with an enzyme, a colorimetric label, fluorescent label, or a radiolabel). The antibody may be a monoclonal or polyclonal antibody. The antibody may be part of a kit (e.g., including instructions for use).

By "fraction of carbamylated albumin" is meant the amount of carbamylated albumin divided by the total amount of albumin (both carbamylated and non-carbamylated) present in a sample (e.g., a biological sample). A fraction may be expressed as a percentage.

By "kidney disease" is meant any disease or condition in which normal renal function is decreased or lost. Kidney disease is typically characterized in five stages (1-5) based on Glomerular filtration rate, where stage 1 indicates slightly diminished function and stage 5 (end-stage renal disease) indicates severely limited function.

By "specifically binds" is meant a compound or antibody which recognizes and binds a target molecule but that does not substantially recognize and bind other molecules in a sample, for example, a biological sample, which naturally includes a the target molecule. In one example, an antibody that specifically binds albumin that is carbamylated at lysine 549 but does not bind uncarbamylated albumin.

By "biological sample" is meant a sample obtained from an individual and used in a diagnostic or monitoring assay. Biological samples encompass, e.g., a clinical sample, cells in culture, cell supernatants, cell lysates, serum, plasma, biological fluid (e.g., urine), and tissue samples. The source of the biological sample may be solid tissue (e.g., from a fresh, frozen, and/or preserved organ, tissue sample, biopsy, or aspirate), blood or any blood constituents, bodily fluids (such as, e.g., urine, lymph, cerebral spinal fluid, amniotic fluid, peritoneal fluid, or interstitial fluid), or cells from any time in gestation or development of the individual. The biological sample may contain compounds that are not naturally intermixed with the tissue in nature, such as preservatives, anticoagulants, buffers, fixatives, nutrients, or antibiotics.

By "control" or "control sample" is meant a biological sample from which a diagnostic or prognostic comparison can be made. For diagnosis of disease or for determining risk of developing disease, an appropriate control sample would be one from a healthy individual (e.g., matched for gender, weight, and/or age) or an average value generated from samples of healthy individuals. For determining disease severity, an appropriate control would include another disease subject or the average of all diseased subjects (e.g., matched for gender, weight, and/or age). Those skilled in the art will be able to determine appropriate control values for conducting the diagnostic and prognostic assays of the invention, depending on the comparison being made.

By "treating" a disease, disorder, or condition in a subject is meant reducing at least one symptom of the disease, disorder, or condition by administrating a therapeutic agent to the subject.

By "treating prophylactically" a disease, disorder, or condition in a subject is meant reducing the frequency of occurrence or severity of (e.g., preventing) a disease, disorder or condition by administering to the subject a therapeutic agent to the subject prior to the appearance of a disease symptom or symptoms.

The term "an effective amount" means the dose needed to effectively treat the physiological effects of a medical condition (e.g., transplant rejection or graft-versus-host disease).

By "subject" is meant a human or non-human animal (e.g., a mammal).

By "carbamylated amino acid" is meant an amino acid modified by a carbamoyl moiety on either its α-amino group or a side chain free amino or sulfhydryl groups (e.g. lysine, arginine, histidine). For example, "carbamylated lysine" is the IUPAC-defined chemical (2S)-2-amino-6-(carbamoylamino)hexanoic acid, also sometimes referred to as homocitrulline.

By "carbamylated protein" is meant a polypeptide modified by a carbamoyl group on a protein side chain amino or free sulfhydryl group, e.g., containing a carbamylated amino acid.

By "cyanate" is meant the chemical with the formula HNCO, and refers to hydrogen cyanate and isocyanate, which are in equilibrium with each other.

Other features and advantages of the invention will be apparent from the following Detailed Description, the drawings, and the claims.

BRIEF DESCRIPTION OF THE DRAWINGS

FIGS. 3A-3D are graphs and tables showing LC-MS/MS identification of an albumin carbamylation site on lysine 549 using pure albumin carbamylated in vitro and digested with Glu-C endoprotease. FIG. 3A is an LC chromatogram showing total ion count for fragmentation products of parent ion m/z=+678.90, corresponding to the predicted m/z for peptide RQIKXQTALVE where X=carbamylated lysine. The peak of interest eluting at 2.8 minutes is indicated by the box. FIG. 3B is an MS/MS spectra for fragmentation products of m/z=+678.90 after collision-induced dissociation for peak eluting at 2.8 min. FIG. 3C is a peptide summary report from a Mascot MS/MS ion search using spectra shown above matched against the SwissProt human protein database. FIG. 3D is a table showing Matches of predicted b-type, c-type, y-type, and z-type daughter ions to ions observed in above spectra. Carbamylated lysine residue X highlighted the fourth item shown in the table (b-type ion 697.4468).

Figure 5:
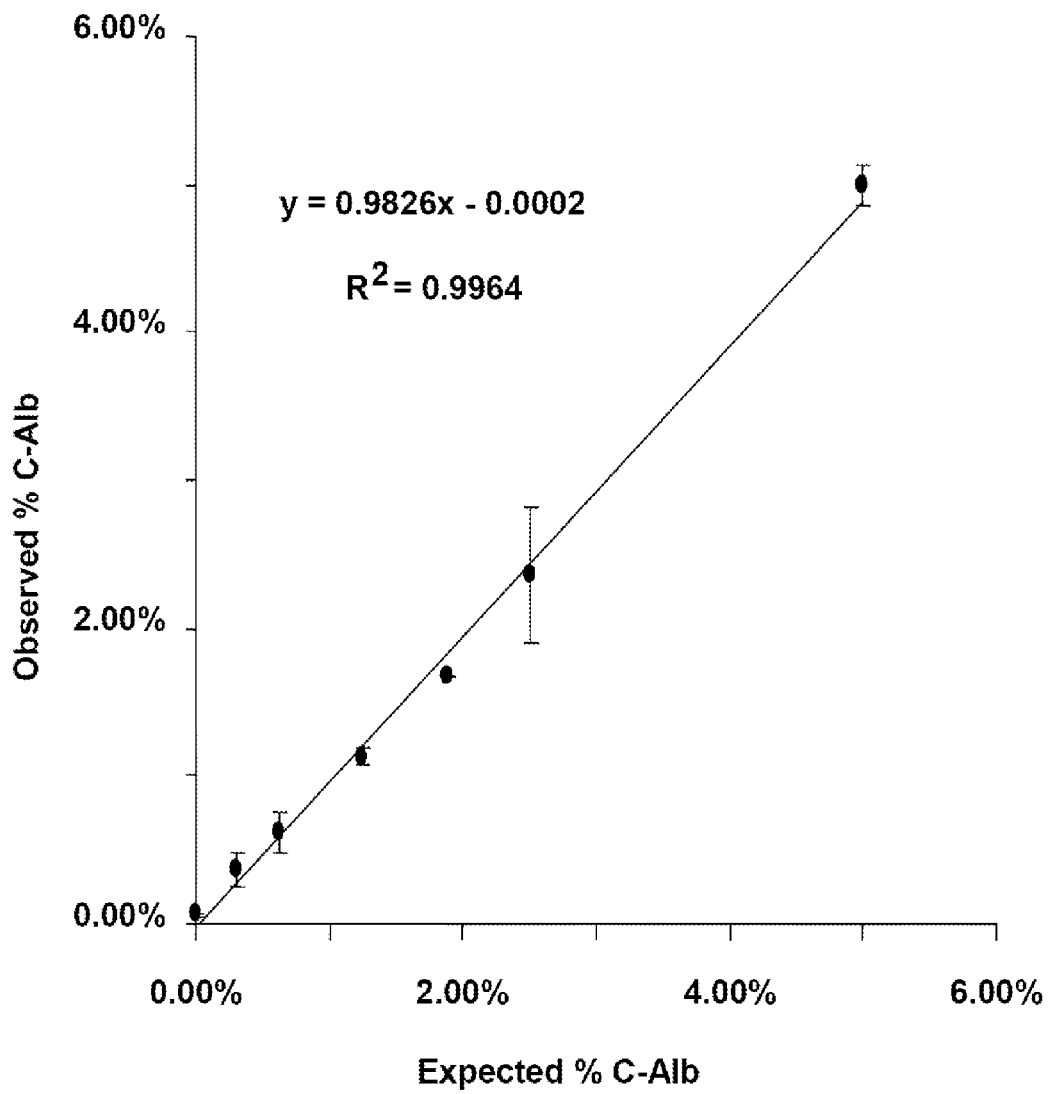

FIG. 5 is a graph showing linearity of % C-Alb assay. Each data point represents the average of three replicate experiments.

Figure 6:
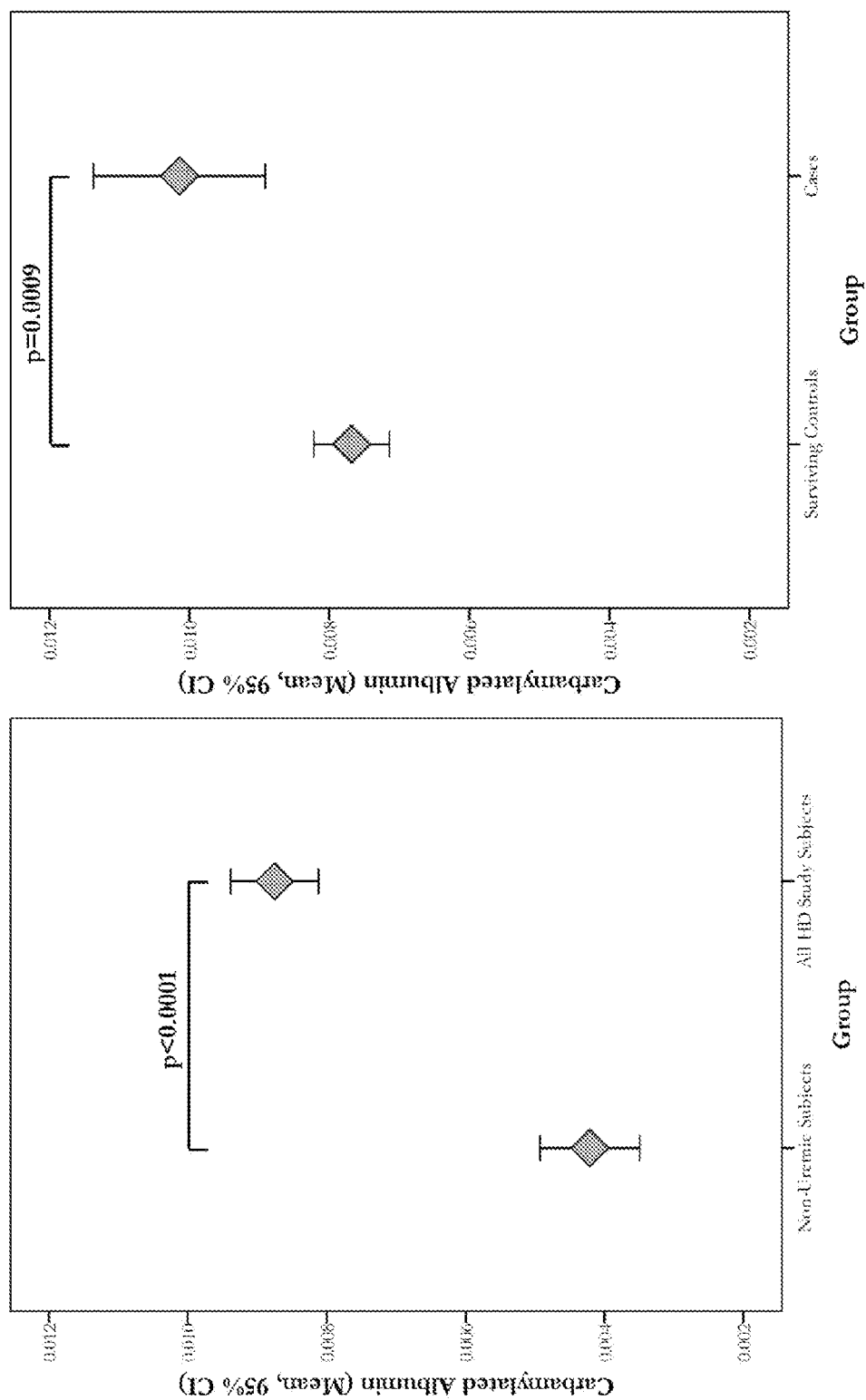

FIG. 6 is a set of graphs. The left panel shows average carbamylated albumin (% C-Alb) levels in control subjects with normal kidney function (n=20) vs. hemodialysis study subjects (n=187). The right panel shows average % C-Alb in hemodialysis cases who died during the 12-month study period (n=88) vs. hemodialysis subjects who survived (n=101). Diamonds show average values, error bars indicate 95% confidence intervals of the mean, Student's t-test P-values shown above.

Figure 7:
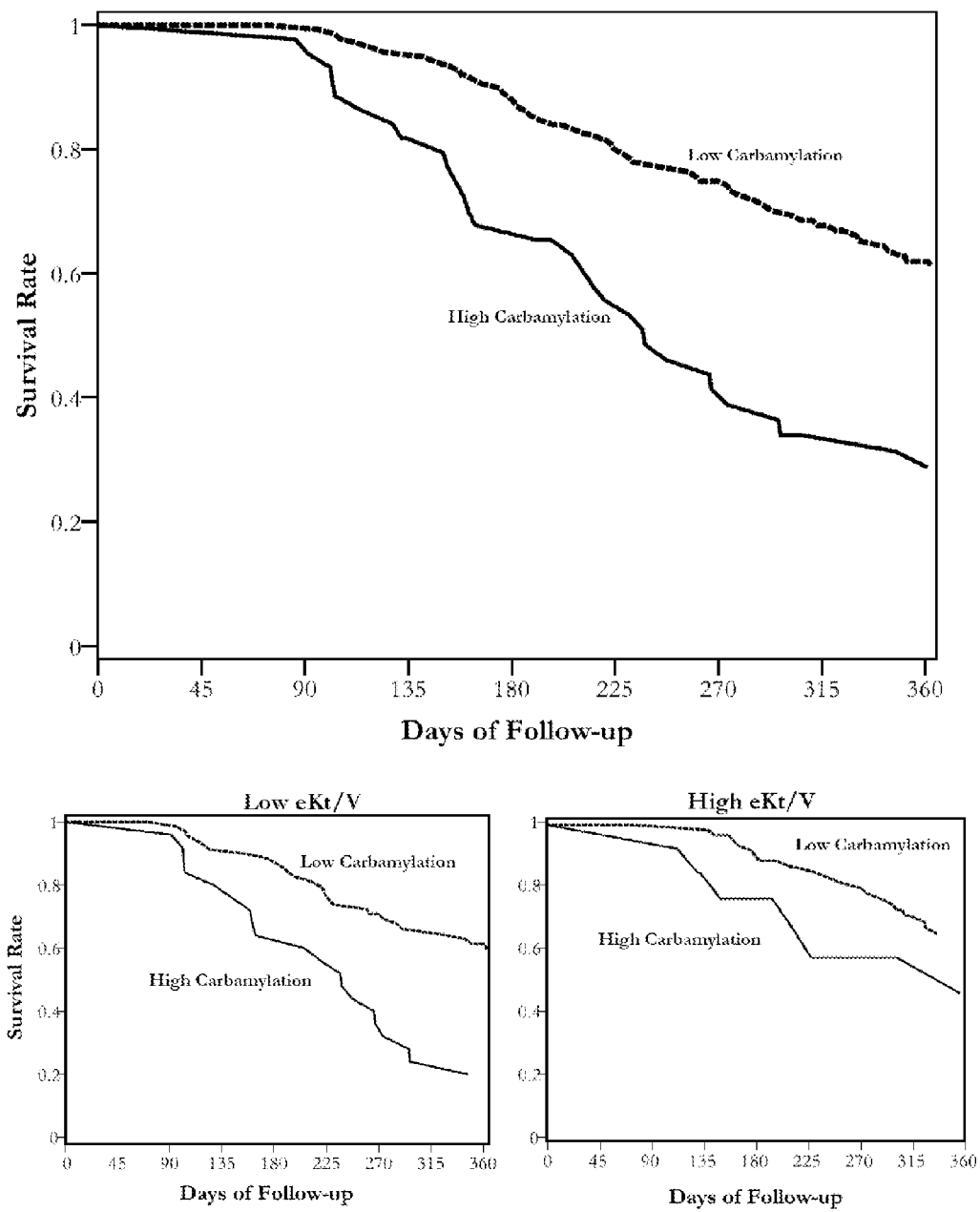

FIG. 7 is a set of graphs showing Kaplan-Meier curve estimates of the incidence of all-cause mortality in patients with low (<1%) versus high (>1%) carbamylated albumin levels. Lower panels shows incidence of all-cause mortality in subjects with high and low C-Alb levels after stratifying for high (>1.3) vs. low (<1.3) equilibrated Kt/V.

Figure 8:
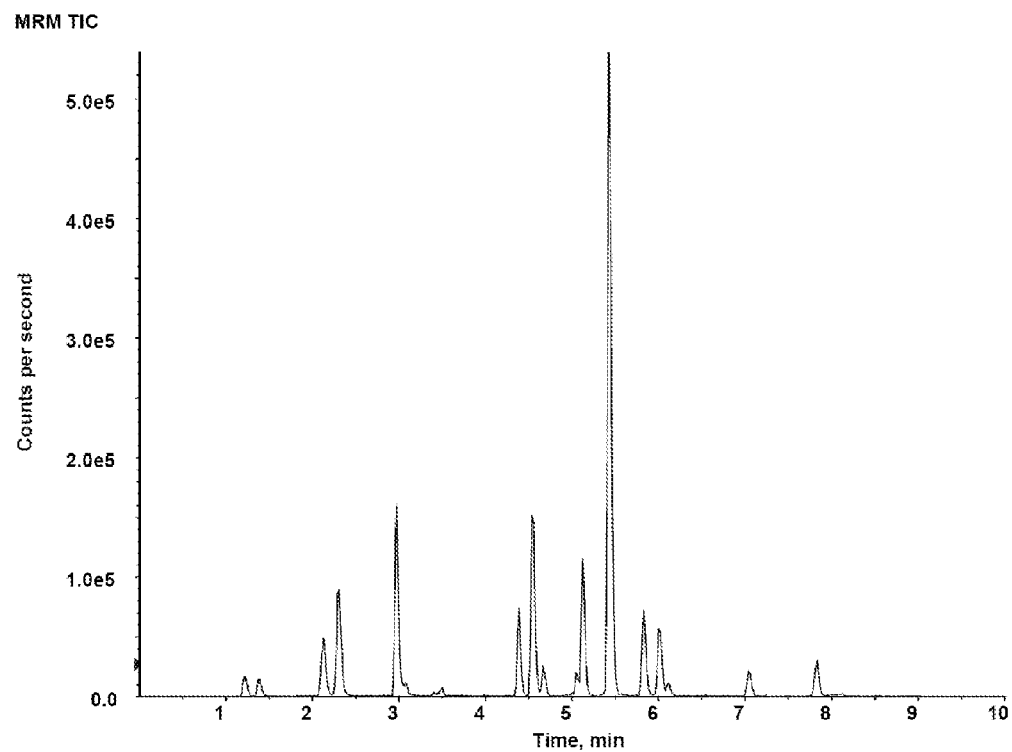

FIG. 8 is an LC chromatogram showing total ion counts for multiple reaction monitors for free and carbamylated serum amino acids and their isotopic standards. X-axis is retention time, y-axis is TIC.

Figure 9A:
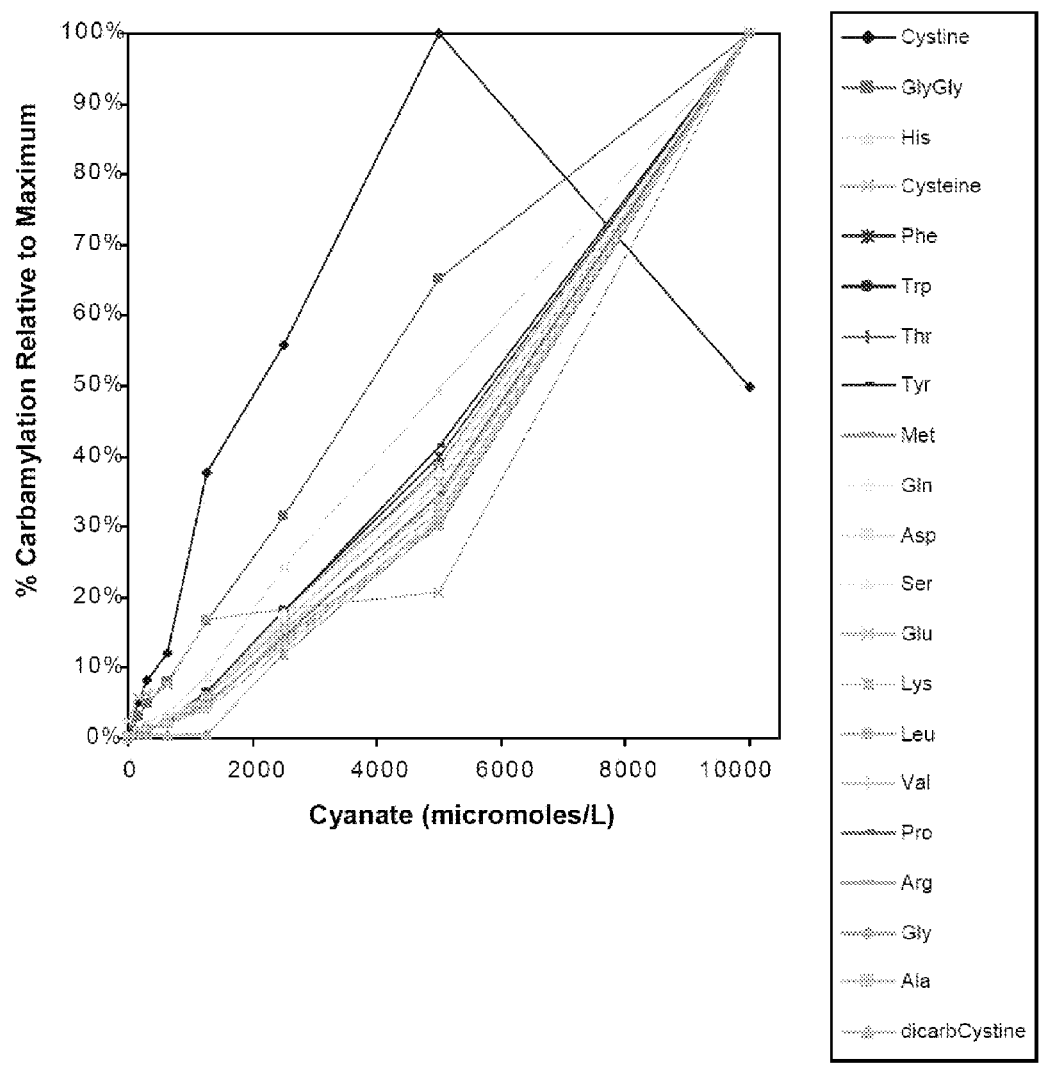
Figure 9B:
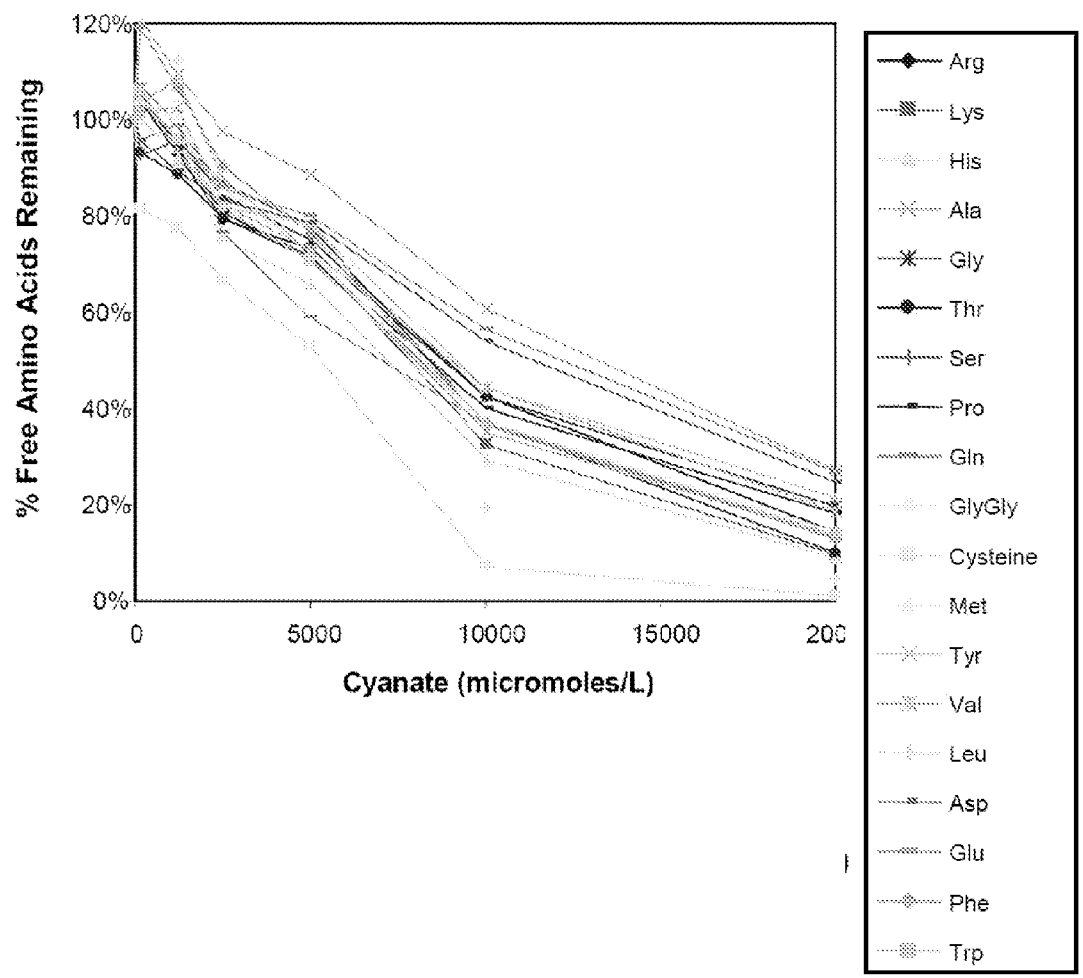

FIGS. 9A and 9B are a set of graphs showing dose-dependent carbamylation and depletion of free amino acids in vitro by increasing concentrations of cyanate. FIG. 9A shows equimolar mixtures of amino acids mixed with increasing concentrations of cyanate overnight. The X-axis is the final concentration of cyanate, and the Y-axis shows % carbamylation relative to the maximum. FIG. 9B shows the same experiments as in FIG. 9A, displaying % unmodified amino acids remaining after reactions with increasing concentrations of cyanate. Each data point in FIGS. 9A and 9B represents average of 3 replicates.

Figure 10:
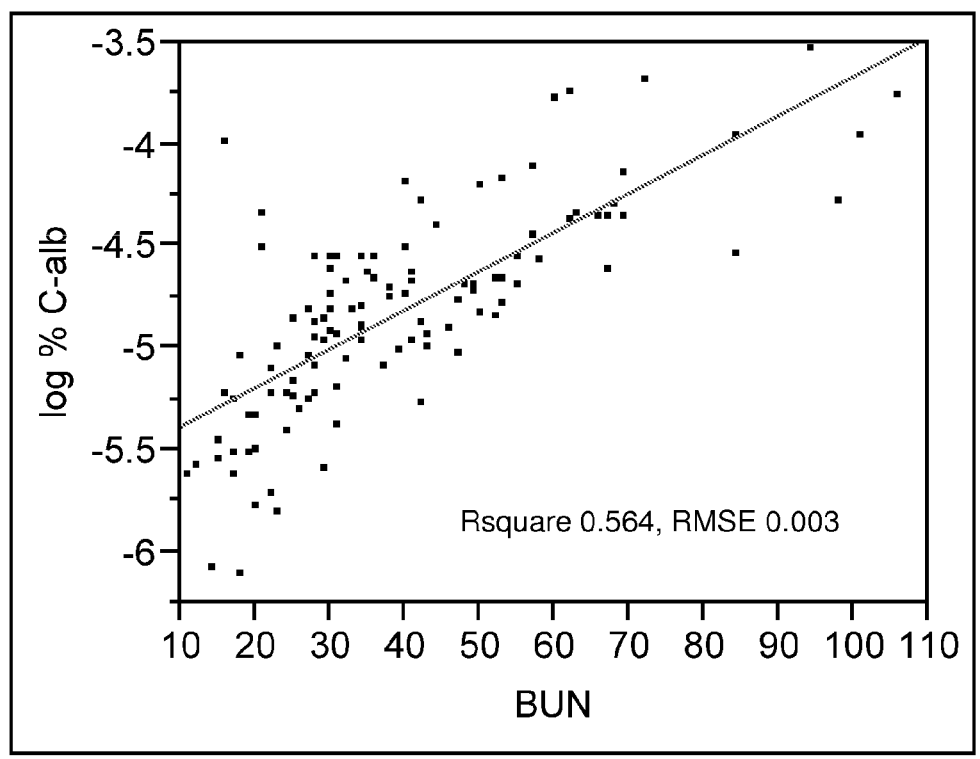

FIG. 10 is a graph showing the association and linear fit between % C-Alb values and blood urea nitrogen concentrations in 115 serum samples from patients with stages 3 and 4 chronic kidney disease not receiving hemodialysis. R-squared and RSME are the coefficient of determination and root mean squared error for the fit using a simple linear model.

Figure 11:
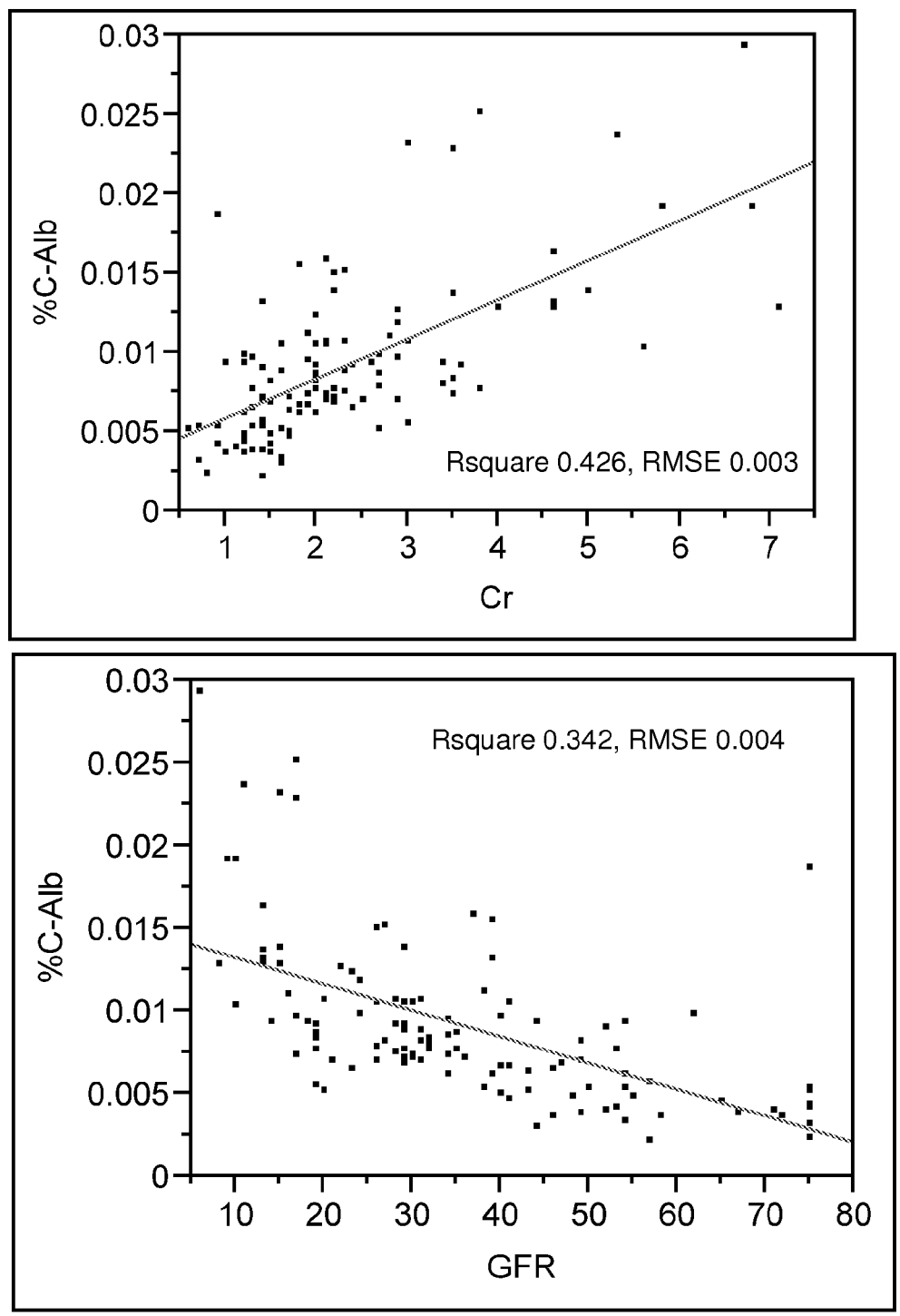

FIG. 11 is a set of two graphs showing the associations and linear fits between % C-Alb values and serum creatinine concentrations (above) and % C-Alb values and estimated glomerular filtration rates (below) in 115 serum samples from patients with stages 3 and 4 chronic kidney disease not receiving hemodialysis. R-squared and RSME are the coefficient of determination and root mean squared error for the fit using a simple linear model.

Figure 12:
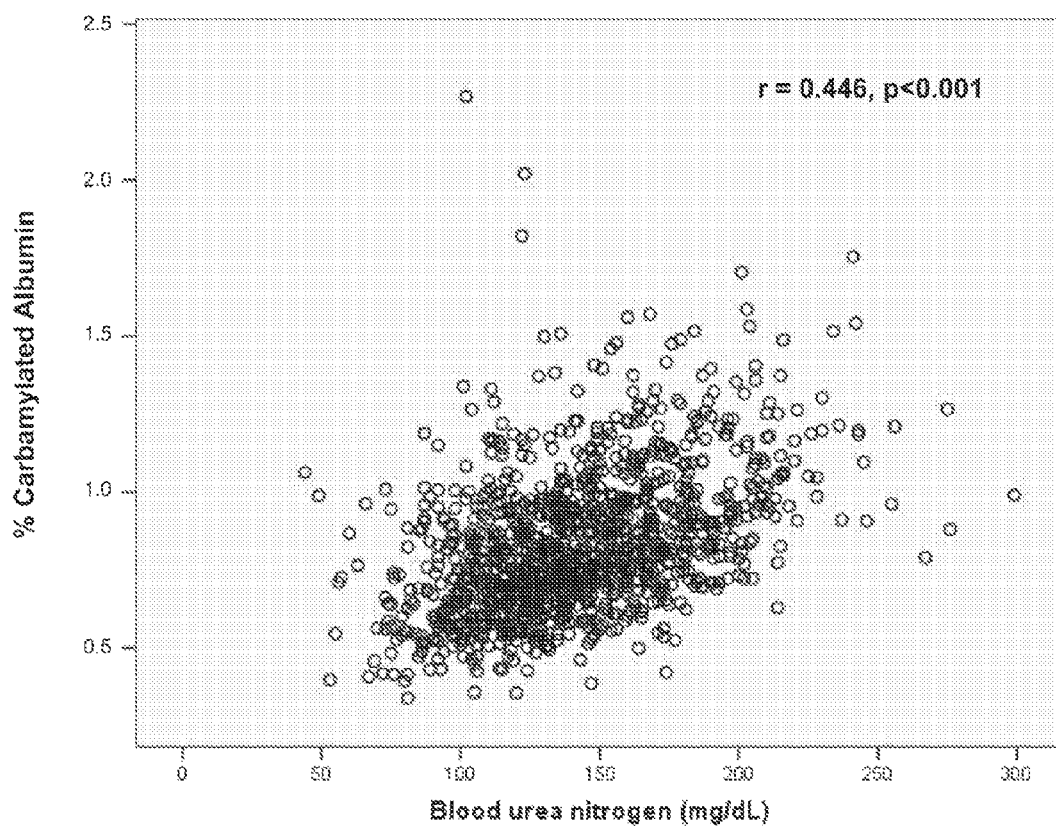

FIG. 12 is a graph showing the association and linear fit between % C-Alb values and blood urea nitrogen concentrations in 1,161 patients with end stage renal disease on hemodialysis. r is the Pearson correlation coefficient and p-value for the correlation coefficient.

DETAILED DESCRIPTION

We have developed diagnostic and prognostic methods for kidney disease (e.g., end-stage renal disease; ESRD) based on the discovery that carbamylation of albumin correlated with both the presence of and mortality rates in kidney disease. We have further discovered that albumin carbamylation can be reduced by administration of certain compounds, including free amino acids, taurine, and dipeptides, thus indicating their usefulness in treatment of kidney disease (e.g., ESRD).

Protein carbamylation is an unavoidable consequence of uremia (Fluckiger et al., *N. Engl. J. Med.* 304:823-7, 1981; Oimomi et al., *N. Engl. J. Med.* 308:655-6, 1983). Carbamylation is the modification of nucleophilic groups on proteins, amino acids, and other biomolecules by cyanate/isocyanate (HNCO), a reactive molecule whose central carbon is susceptible to non-enzymatic nucleophilic attack from electron donors such as primary amines and thiols (Stark et al., *Biochemistry* 4:1030-6, 1965; Stark et al., *J. Biol. Chem.* 235:3177-81, 1960). Patients with renal failure have shown to have elevated concentrations of plasma cyanate (Nilsson et al., *Clin. Chem.* 42:482-3, 1996) and as a result developed increased concentrations of carbamylated proteins and amino acids (Berlyne et al., *Nephron* 79:125-30, 1998; Kraus et al., *J. Lab. Clin. Med.* 131:425-31, 1998; Kraus et al., *Kidney Int. Suppl.* 78:S102-7, 2001). Elevated concentrations of plasma cyanate in these patients are most likely due to their failure to eliminate cyanate in the urine, as well as the accumulation of the chemical precursors of cyanate: urea, cyanide, and thiocyanate (Hasuike et al., *Nephrol. Dial. Transplant.* 19:1474-9, 2004; Koyama et al., *Nephrol. Dial. Transplant.* 12:1622-8, 1997; Nilsson et al., *Clin. Chem.* 42:482-3, 1996). Urea synthesis provides a thermodynamically stable means of sequestering ammonia nitrogen prior to disposal; however, urea is in equilibrium with trace concentrations of reactive cyanate. In addition to urea, isocyanate may be produced in humans as a byproduct of cyanide detoxification. Cyanide is a toxin that enters the body through inhalation of cyanide gas from tobacco smoke and air pollution, through the consumption of cyanogenic foods such as cassava root, or by the chlorination of glycine by myeloperoxidase (Ebbs et al., *Curr. Opin. Biotechnol.* 15:231-6, 2004; Lemma et al., *Chem. Res. Toxicol.* 22:1622-8, 2009; Wilson et al., *Fundam. Appl. Toxicol.* 3:397-9, 1983; Zgiczynski et al., *Biochim. Biophys. Acta* 567:309-14, 1979). Cyanide is primarily detoxified by enzymatic transsulfation to thiocyanate. Thiocyanate is normally eliminated in the urine; however, thiocyanate may be converted by myeloperoxidase into cyanate by two separate pathways (Lemma et al., *Chem. Res. Toxicol.* 22:1622-8, 2009; Wang et al. *Nat. Med.* 13:1176-84, 2007). Patients with ESRD have not only chronically elevated blood urea concentrations, they also have increased concentrations of whole blood cyanide and plasma thiocyanate (Hasuike et al., *Nephrol. Dial. Transplant.* 19:1474-1479, 2004; Koyama et al., *Nephrol. Dial. Transplant.* 12:1622-28, 1997; Nilsson et al., *Clin. Chem.* 42:482-3, 1996), and thus multiple contributors to isocyanate production and carbamylation are increased in patients with renal insufficiency.

Carbamylation occurs at the N-terminus or side chains of proteins in vivo (Stark et al., *J. Biol. Chem.* 235:3177-81, 1960). Because carbamylation represents a spontaneous chemical reaction proportional to isocyanate concentrations, we believe that levels of carbamylated proteins should represent a time-averaged indicator of blood isocyanate levels, analogous to glycation of hemoglobin (% Hb $A_{1c}$) and its relationship to average glucose levels in patients with diabetes mellitus (Nathan et al., *Diabetes Care* 31:1473-8, 2008; Nathan et al., *N. Engl. J. Med.* 310:341-6, 1984). Prior investigations of protein carbamylation in humans have focused on carbamylated hemoglobin (Fluckiger et al., *N. Engl. J. Med.* 304:823-7, 1981), but its levels have shown only modest correlations with time-averaged BUN or eKt/V (Davenport et al., *Kidney Int.* 50:1344-51, 1996; Hasuike et al., *Nephron* 91:228-34, 2002; Smith et al., *Clin. Chim. Acta.* 178:297-303, 1988; Tarif et al., *Am. J. Kidney Dis.* 30:361-5, 1997) or no correlation at all (Ballon et al., *Kidney Int.*

53:488-95, 1998). Erythrocyte lifespan in patients with ESRD, however, is significantly altered by chronic uremia, red cell damage during dialysis, and variable rates of erythropoiesis which depend upon their treatment regimens with (and response to) exogenous erythropoietin (Nakao et al., *Intern. Med.* 37:826-30, 1998; Uzu et al., *Ther. Apher. Dial.* 13:89-94, 2009). These factors make the age of red cells, and the hemoglobin they contain, heterogeneous and unpredictable in these patients, and thus an unreliable marker of time-averaged carbamylation.

Because free amino acids all contain at least one α-amino group and additional nucleophiles depending upon their side chain and because free amino acids are also susceptible to carbamylation (Stark et al., *J. Biol. Chem.* 235:3177-81, 1960), we predicted that endogenous free amino acids compete with proteins for carbamylation. Together, these two observations suggested that elevated urea may not be the only determinant of protein carbamylation, and prompted us to wonder whether endogenous scavengers of reactive isocyanate also play a role.

Based upon our hypothesis that protein carbamylation represents a time-averaged indicator of average urea concentrations and is a direct contributor to uremia-associated complications, we therefore asked whether protein carbamylation could be measured on long-lived circulating serum protein, albumin, and if so, whether its values were uniquely informative about the risk of mortality in ESRD patients. Further, we hypothesized that protein carbamylation may be inhibited by circulating free amino acids and other strong physiologic nucleophiles such as taurine, cysteamine, and glycylglycine, and that patients deficient in cyanate-scavenging amino acids (due to protein-energy wasting, hemodialysis, or a combination of the two) will be especially prone to protein carbamylation and its associated risk of CVD.

In the present studies, we developed a novel assay to quantify the carbamylation of proteins in vivo and applied that assay to subjects with ESRD, a population of patients highly susceptible to protein carbamylation. We found that the % C-Alb out-performed the gold standard for measuring dialysis adequacy, eKt/V, in predicting the risk of all-cause mortality. Further, we found strong evidence of a competition for carbamylation between free amino acids and albumin in vivo. Finally, we demonstrated that select amino acids and related bio-organic nucleophiles could prevent albumin carbamylation. Together, our results have identified a new assay for a process that may be pathogenic in patients with ESRD and have described a novel mechanism for its prevention.

The strong and independent prediction of mortality by % C-Alb raises the question of how protein carbamylation may adversely impact health. In general, this non-enzymatic post-translational modification could disrupt the normal function of proteins, be it catalysis, structural support, signaling, or regulatory. Because urea is present in equimolar amounts intracellularly, carbamylation could also alter the folding process in the endoplasmic reticulum or modify normal protein turnover (e.g., by masking lysines that would otherwise be ubiquitinated). On extracellular proteins, carbamylation could mask epitopes critical for ligand-receptor interactions or create neo-epitopes for antigenic recognition. As one example, carbamylation of LDL was recently shown to convert this protein into a ligand for the macrophage scavenger receptor A1 (Nakao et al., *Intern. Med.* 37:826-30, 1998), which in turn, promoted pro-atherogenic functions. Finally, protein carbamylation could be a marker of total isocyanate load, which may be toxic in other ways, e.g., by oligomerizing to cyanuric acid, which was recently implicated in melamine tainting (Ingelfinger J R, *N. Engl. J. Med.* 359:2745-8, 2008).

The toxicity of urea is controversial, and over the years, the idea that it represents a critical uremic toxin was largely dismissed for several reasons. First, randomized trials testing the effect of extra dialysis, as measured by delivered eKt/V, have shown no survival advantage (Eknoyan et al., *N. Engl. J. Med.* 347:2010-9, 2002; Paniagua et al., *J. Am. Soc. Nephrol.* 13:1307-20, 2002). However, this may be because the target variable eKt/V is subject to confounding by a number of factors, including the movement of urea into and out of cells, especially after a dialysis session, the effect of weight on the (V) variable, and the failure to account for differences in total body water between subjects. In this regard, more recent studies with daily dialysis, as opposed to 3×/wk, the standard prescription, do show an unexplained patient benefit (Ayus et al., *J. Am. Soc. Nephrol.* 16:2778-88, 2005; Pauly R P, *Adv. Chronic Kidney Dis.* 16:169-72, 2009). Second, a 40-year-old trial that is often cited observed that patients loaded with urea during their dialysis treatments failed to develop deterioration of their clinical status (Johnson et al., *Mayo Clin. Proc.* 47:21-9, 1972). This study, however, was limited to the observation of acute symptoms of uremia, not long-term outcomes or mortality. Only three subjects were actually involved, and the longest follow-up period was 90 days. Thus, these past studies and the conclusions that can be drawn from them should be reconsidered in light of new evidence. Our data suggest that current measures of total body urea load (or urea removal) do not adequately reflect the harm mediated by its overload.

Analogous to the utility of measuring glycated hemoglobin $A_{1c}$ to determine long-term glucose control in diabetes mellitus, % C-Alb may provide a clearer depiction of urea load than a BUN measurement that can fluctuate 40-70% around any given dialysis session. Moreover, BUN is a complex variable, reflecting not only the disposal rate through urinary excretion or dialysis, but also the formation rate as nitrogenous waste from protein consumption fluxes through the urea cycle. Low BUN (<10 mg/dl) is a common laboratory sign of protein malnutrition (Fouque et al., *Kidney Int.* 73:391-8, 2008). In turn, malnutrition is strongly associated with increased morbidity and mortality in ESRD (Kalantar-Zadeh et al., *Am. J. Kidney Dis.* 38:1251-63, 2001; Stenvinkel et al., *Kidney Int.* 55:1899-911, 1999). % C-Alb may better address the confounding effect of protein malnutrition because free amino acids also fall in malnourished individuals, thus reducing the competition for cyanates. Stated differently, both poor disposal of urea and protein malnutrition would be predicted to enhance the formation of C-Alb whereas these factors would have opposing effects on BUN. Our experiments demonstrating that free amino acids act as cyanate scavengers and protect albumin from carbamylation, combined with our observation that carbamylation is increased in renal failure patients with low serum amino acids, indicate that enhanced protein carbamylation may be a mechanism by which protein malnutrition promotes poor health in dialysis patients.

Diagnostic and Prognostic Methods

Based on the discovery that the fraction of albumin carbamylated at lysine 549 correlates with increased disease severity and mortality in patient suffering from kidney disease, the present invention features methods that involve measuring one specific site of protein carbamylation, e.g., of albumin at lysine 549, in samples taken from subjects. In certain embodiments, the subject may have, be at increased risk of having, or be suspected of having kidney disease. Exemplary methods for detecting protein carbamylation are described below.

These methods may, in certain embodiments, be combined with measurements of free amino acids in the subject. As set forth below, free amino acid levels correlate negatively with c-Alb levels and levels of carbamylated free amino acids correlate positively with c-Alb levels. Based on these results, we believe that free amino acid levels can also be used to diagnose the presence of kidney disease, predict the risk of developing kidney disease, or determine the severity of kidney disease.

Measurement of Carbamylated Protein

Carbamylated albumin may be measured using any analytically capable method. As described herein, diagnosis of kidney disease, an increased risk of developing or propensity towards kidney disease, or severity of kidney diseases (e.g., increased risk of mortality. In these assays, the percent fraction of carbamylated albumin (e.g., at lysine 549) relative to non-carbamylated albumin is measured in a subject.

Standard methods may be used to measure levels of carbamylated albumin in any bodily fluid, including, but not limited to, urine, serum, plasma, saliva, amniotic fluid, or cerebrospinal fluid. Such methods include immunoassay, enzymatic immunoassay, ELISA, "sandwich assays," immunoturbidimetry, immunonephelometry, western blotting using antibodies specifically directed to carbamylated albumin, immunodiffusion assays, agglutination assays, fluorescent immunoassays, protein A or G immunoassays, and immunoelectrophoresis assays and quantitative enzyme immunoassay techniques such as those described in Ong et al. (*Obstet. Gynecol.* 98:608-11, 2001) and Su et al. (*Obstet. Gynecol.* 97:898-904, 2001). In certain embodiments, an antibody or ELISA assay is used, including the sandwich or double antibody assay. A number of variations of these assays exist, all of which are contemplated by the present invention. For example, in a typical sandwich assay, unlabeled antibody that recognizes the antigen (i.e., carbamylated albumin) is immobilized on a solid phase, e.g. microtiter plate, and the sample to be tested is added. After a certain period of incubation to allow formation of an antibody-antigen complex, a second antibody, labeled with a reporter molecule capable of inducing a detectable signal, is added and incubation is continued to allow sufficient time for binding with the antigen at a different site, resulting with a formation of a complex of antibody-antigen-labeled antibody. The presence of the antigen is determined by observation of a signal which may be quantitated by comparison with control samples containing known amounts of antigen. To determine the fraction of carbamylated albumin, it may be desired to measure total albumin levels using a similar or different assay.

Other methods useful for determining the fraction of carbamylated albumin include chromatographic separation of carbamylated and non-carbamylated intact albumin followed by detection of separated fractions by protein-detection methods including UV or fluorescence spectroscopy, colorimetry, immunoassay, or mass spectrometry-based methods. Carbamylated and non-carbamylated albumin proteins may also be proteolytically digested, separated chromatographically, and the carbamylated and non-carbamylated peptides may be detected by mass spectrometry. Examples of such methods are described herein. Briefly, serum proteins are digested with glutamyl endoproteinase (Glu-C), liberated carbamylated albumin and non-carbamylated albumin peptides are separated chromatigraphically, and these two peptides are detected and quantified by tandem mass spectrometry, which resolves the peptides based upon their different chemical composition and corresponding mass difference.

The method may optionally include a further measurement of free amino acids in such subjects, as described below.

Measurement of Free Amino Acids

Amino acid measurements can be performed using any available method, e.g., those known in the art. In certain embodiments, as described below, amino acid levels are measured using mass spectroscopy and are measured against isotopic amino acid standards. Methods for measuring free are also described, for example, in Scriver et al., *Metabolism* 34:868-73, 1985 and McLaughlan et al., *Can. J. Biochem. Physiol.* 39:1669-74, 1961.

Antibodies

The invention also features an antibody that is capable of specifically binding carbamylated albumin (e.g., carbamylated at lysine 549). These antibodies are useful for detecting carbamylated albumin in a serum sample to determine the fraction of carbamylated albumin in a subject.

Antibodies (e.g., monoclonal, polyclonal, poly-specific, or mono-specific antibodies) against carbamylated albumin can be made, e.g., using any of the numerous methods for making antibodies known in the art. In one example, the relevant albumin sequence containing carbamylated lysine 549 is produced as a C-terminal fusion with glutathione S-transferase (GST) (Smith et al., *Gene* 67:31-40, 1988). The fusion protein is purified on glutathione-Sepharose beads, eluted with glutathione, cleaved with thrombin (at an engineered cleavage site), and purified for immunization of rabbits. Primary immunizations are carried out with Freund's complete adjuvant and subsequent immunizations with Freund's incomplete adjuvant. Antibody titers are monitored by Western blot and immunoprecipitation analyses using the thrombin-cleaved protein fragment of the GST fusion protein. Immune sera are affinity purified using CNBr-Sepharose-coupled protein. Antiserum specificity can be determined using a panel of unrelated GST proteins.

As an alternate or adjunct immunogen to GST fusion proteins, peptides corresponding to relatively unique immunogenic regions of a polypeptide of the invention can be generated and coupled to keyhole limpet hemocyanin (KLH) through an introduced C-terminal lysine. Antiserum to each of these peptides is similarly affinity purified on peptides conjugated to BSA, and specificity is tested by ELISA or Western blot analysis using peptide conjugates, or by Western blot or immunoprecipitation using the polypeptide expressed as a GST fusion protein.

Alternatively, monoclonal antibodies that specifically bind carbamylated albumin can be prepared using standard hybridoma technology (see, e.g., Kohler et al., *Nature* 256: 495-7, 1975; Kohler et al., *Eur. J. Immunol.* 6:511-9, 1976; Kohler et al., *Eur. J. Immunol.* 6:292-5, 1976; Hammerling et al., *Monoclonal Antibodies and T Cell Hybridomas*, Elsevier, N.Y., 1981). Once produced, monoclonal antibodies can also be tested for specific recognition by Western blot or immunoprecipitation analysis. Alternatively, monoclonal antibodies can be prepared using the polypeptide of the invention described above and a phage display library (Vaughan et al., *Nat. Biotechnol.* 14:309-14, 1996).

Epitopic fragments can be generated by standard techniques, e.g., using PCR and cloning the fragment into a pGEX expression vector. Fusion proteins are expressed in *E. coli* and purified using a glutathione agarose affinity matrix. To minimize potential problems of low affinity or specificity of antisera, two or three such fusions are generated for each protein. These fusions can then be carbamylated, e.g., using any of the methods described herein. Each fusion is then injected into at least two rabbits. Antisera are raised by injections in a series, and can include, for example, at least three booster injections.

In order to generate polyclonal antibodies on a large scale and at a low cost an appropriate animal species can be chosen. Polyclonal antibodies can be isolated from the milk or colostrum of, e.g., immunized cows. Bovine colostrum contains 28 g of IgG per liter, while bovine milk contains 1.5 g of IgG per liter (Ontsouka et al., *J. Dairy Sci.* 86:2005-11, 2003). Polyclonal antibodies can also be isolated from the yolk of eggs from immunized chickens (Sarker et al., *J. Pediatr. Gastroenterol. Nutr.* 32:19-25, 2001).

Multiple adjuvants are approved for use in dairy cows. Adjuvants useful in this invention include, but are not limited to, Emulsigen®, an oil-in-water emulsified adjuvant, Emulsigen®-D, an oil-in-water emulsified adjuvant with DDA immunostimulant, Emulsigen®-P, an oil-in-water emulsified adjuvant with co-polymer immunostimulant, Emulsigen®-BCL, an oil-in-water emulsified adjuvant with block co-polymer immunostimulant, Carbigen™, a carbomer base, and Polygen™, a co-polymer base. All of the listed adjuvants are commercially available from MVP Laboratories in Omaha, Nebr.

Useful antibodies can be identified in several different screening assays. First, antibodies are assayed by ELISA to determine whether they are specific for the immunizing antigen (i.e., carbamylated albumin). Using standard techniques, ELISA plates are coated with immunogen, the antibody is added to the plate, washed, and the presence of bound antibody detected by using a second antibody specific for the Ig of the species in which the antibody was generated.

A functional in vitro assay can be used to screen antibodies e.g., a neutralizing assay based on monocyte-derived dendritic cells.

Direct measurements of bovine immunoglobulin in ileal fluid in human subjects have shown that significant amounts of immunoglobulin survive transit through the stomach and small intestine (Warny et al., *Gut* 44:212-7, 1999). Methods have also been described to formulate avian immunoglobulin (IgY) for GI delivery (Kovacs-Nolan et al., *Immunol. Methods* 296:199-209, 2005).

Determination of Risk

Figure 1:
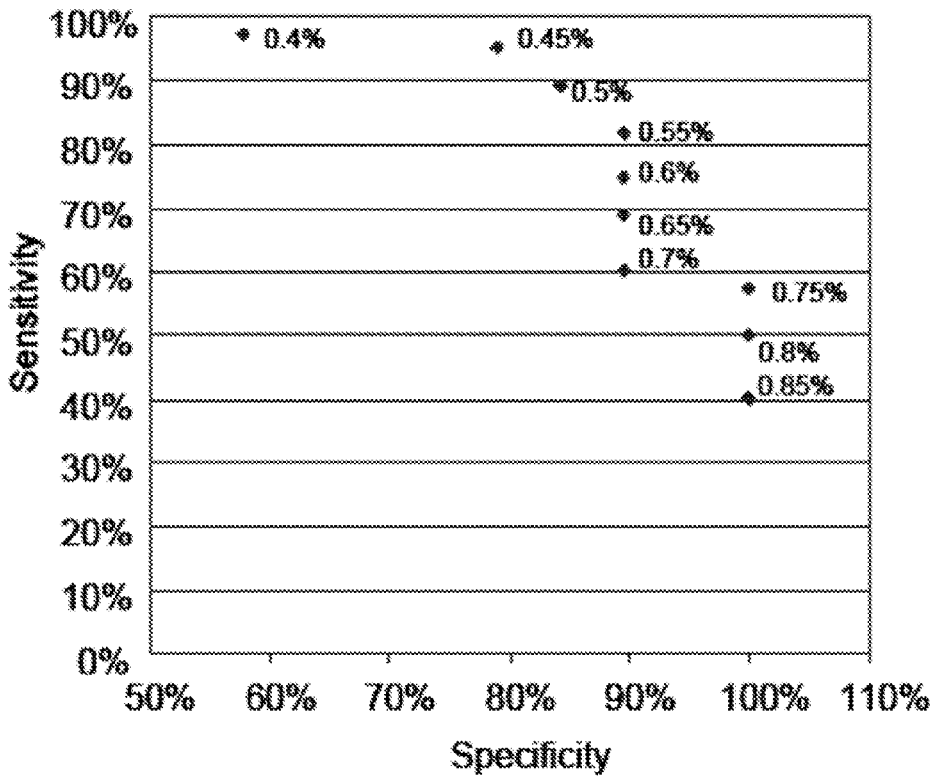
FIG. 1 is a graph referred to as a receiver-operator curve. It graphically depicts the quantitative relationship between the diagnostic sensitivity and specificity of a qualitative (positive/negative) test when using different diagnostic threshold values. In this instance, it compares the sensitivity and specificity of the % C-Alb test at various diagnostic thresholds in differentiating kidney disease from normal kidney function, when applied to a cohort of 187 ESRD patients and 19 controls with normal kidney function.

The method can be used to determine levels of carbamylated albumin that are above a threshold level and are diagnostic of severity of or increased mortality in kidney disease. The normal level of albumin carbamylation is on average 0.42% and is generally less than 0.50% or 0.60%. In preferred embodiments, a carbamylation above a specific threshold may be diagnostic for kidney disease. For example, when we measured % C-Alb values in a cohort of 115 patients with stage 3 or 4 chronic kidney disease who were not receiving hemodialysis, % C-Alb was strongly correlated with BUN, creatinine, and estimated glomerular filtration rates (FIGS. 10 and 11). Furthermore, when we measured % C-Alb concentrations in 1,161 patients with end-stage renal disease and correlated % C-Alb results with pre-hemodialysis BUN concentrations, we again found strong linear relationship between the variables (FIG. 12). Lastly, when we measured serum % C-Alb values in 187 patients with end-stage renal disease and compared them to concentrations in 19 control patients with no evidence of kidney disease, a % C-Alb of 0.50% was 89% sensitive and 84% specific for the detection of kidney disease. By varying the threshold, furthermore, the test could be optimized for increased sensitivity or specificity (FIG. 1). Together, these results indicate that serum % C-Alb values are a diagnostic indicator of time-averaged blood urea concentrations and time-averaged renal function.

Figure 2:
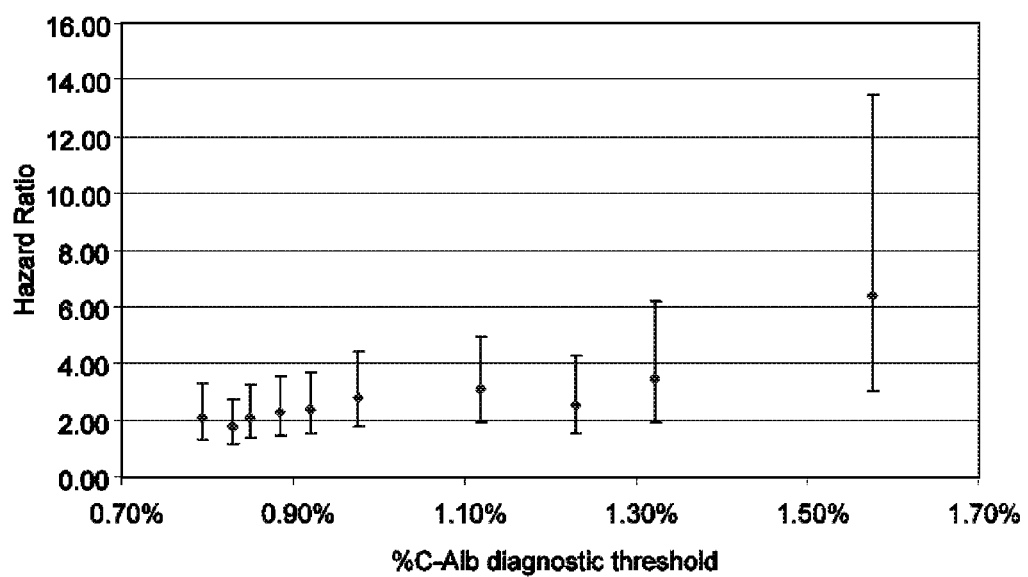
FIG. 2 is a graph showing the risk of death associated with % C-Alb values above specific thresholds when applied to 187 ESRD cases and control subjects. The data points and error bars show univariate hazard ratios and their 95% confidence intervals at different diagnostic cut-points.
Figure 3A:
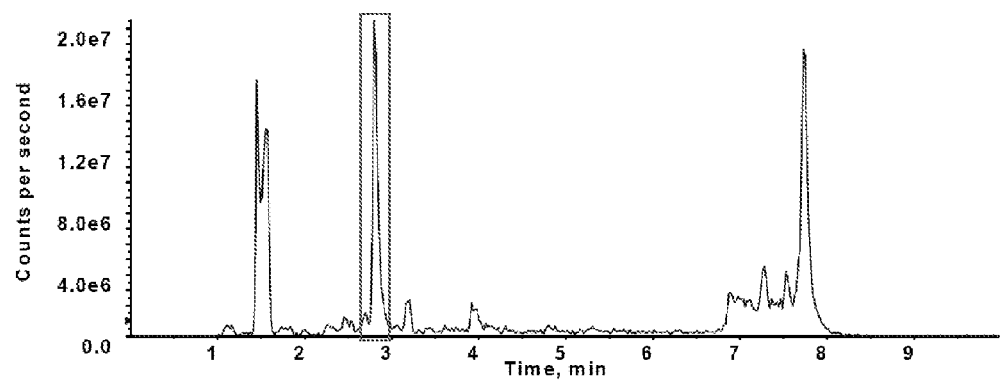
Figure 3B:
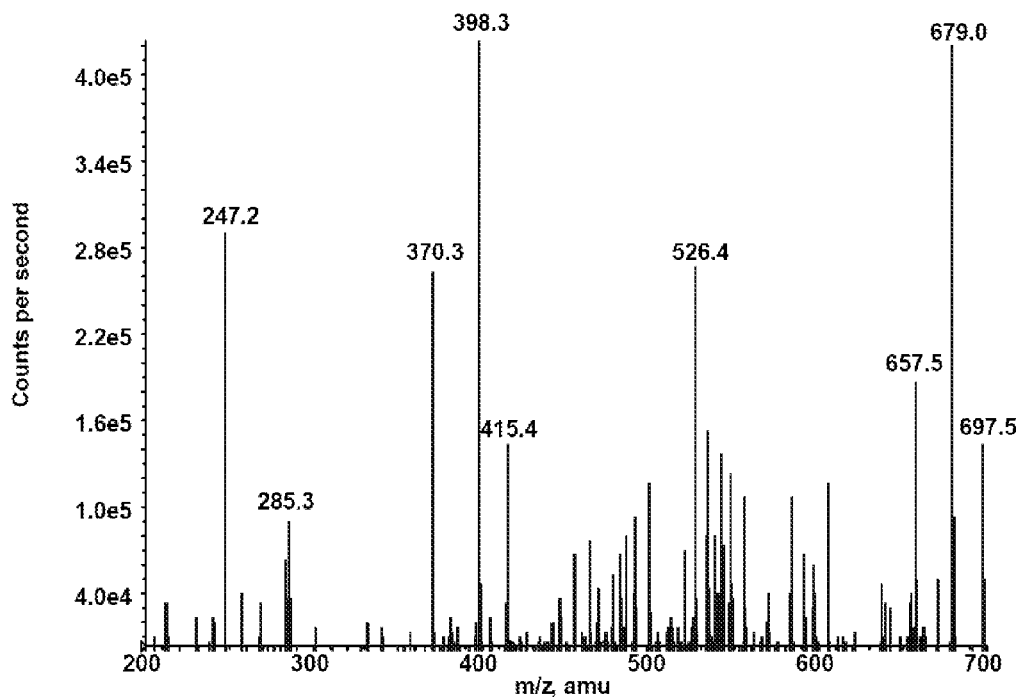

Albumin carbamylation (% C-Alb) above a specific threshold may also be prognostic for increased risk of morality. For example, % C-Alb values above 0.85% are associated with an estimated hazard ratio of 2.10 (1.35-3.26 95% CI), and this risk increases at higher % C-Alb thresholds (FIG. 2).

Amino Acid Treatment of Kidney Disease

Because carbamylation may be linked directly to kidney disease pathology, the present invention features methods of treating kidney disease (e.g., ESRD) by administration of a composition that is capable of reducing protein carbamylation in a subject.

In particular embodiments, carbamylation can be reduced by administration of an amino acid or an amino acid dipeptide. Exemplary amino acids that may be used in the methods of the invention include glycylglycine, taurine, cysteamine, cysteine, histidine, arginine, gluthathione, lysine, glycine, glutamine, tryptophan, alanine, valine, proline, leucine, and glutamate, or a combination thereof (e.g., cysteine and cysteamine).

The composition capable of reducing carbamylation can be administered by a variety of methods known in the art. As will be appreciated by the skilled artisan, the route and/or mode of administration will vary depending upon the desired results. Administration may be parenteral, intravenous, intrathecal, subcutaneous, oral, topical, local, or as therapeutic additives to hemodialysis solutions. Intravenous delivery by continuous infusion is one exemplary method for administering the composition. The therapeutic composition may be in the form of a solution, a suspension, an emulsion, an infusion device, or a delivery device for implantation, or it may be presented as a dry powder to be reconstituted with water or another suitable vehicle before use. The composition can be in the form of a pill, tablet, capsule, liquid, or sustained release tablet for oral administration; or a liquid for intravenous, intrathecal, subcutaneous or parenteral administration; or a polymer or other sustained release vehicle for local administration.

Methods well known in the art for making formulations are found, for example, in "Remington: The Science and Practice of Pharmacy" (20th ed., ed. A. R. Gennaro A R., 2000, Lippincott Williams & Wilkins, Philadelphia, Pa.). Formulations for parenteral administration may, for example, contain excipients, sterile water, saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful delivery systems include ethylene-vinyl acetate copolymer particles, osmotic pumps, intrathecal pumps, implantable infusion systems, and liposomes. The concentration of the compound in the formulation varies depending upon a number of factors, including the dosage of the drug to be administered, and the route of administration.

To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., *J. Neuroimmunol.* 7:27-41, 1984). Pharmaceutically acceptable carriers include sterile aqueous solutions or dispersions and sterile powders for the extemporaneous preparation of sterile injectable solutions or dispersion. The use of such media and agents for pharmaceutically active substances is known in the art and is included in the invention except where any conventional media or agent is incompatible with the active compound. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. For example, the antibodies of the invention may be administered once or twice weekly by subcutaneous injection or once or twice monthly by subcutaneous injection.

It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

The phrases "parenteral administration" and "administered parenterally" as used herein mean modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrastemal injection and infusion. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Compositions of the invention may also contain adjuvants such as preservatives, wetting agents, emulsifying agents and dispersing agents. Prevention of presence of microorganisms may be ensured both by sterilization procedures, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

When the compounds of the present invention are administered as pharmaceuticals, to humans and animals, they can be given alone or as a pharmaceutical composition containing, for example, 0.001 to 90% (more preferably, 0.005 to 70%, such as 0.01 to 30%) of active ingredient in combination with a pharmaceutically acceptable carrier.

For intravenous or intrathecal delivery or direct injection or as an additive to hemodialysis solution, the composition must be sterile and fluid to the extent that the composition is deliverable by syringe. In addition to water, the carrier can be an isotonic buffered saline solution, ethanol, polyol (for example, glycerol, propylene glycol, and liquid polyetheylene glycol, and the like), and suitable mixtures thereof. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art. Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A physician or veterinarian having ordinary skill in the art can readily determine and prescribe the effective amount of the pharmaceutical composition required. For example, the physician or veterinarian can start doses of the compounds of the invention employed in the pharmaceutical composition at levels lower than that required in order to achieve the desired therapeutic effect and gradually increase the dosage until the desired effect is achieved. In general, a suitable daily dose of a composition of the invention will be that amount of the compound which is the lowest dose effective to produce a therapeutic effect. Such an effective dose will generally depend upon the factors described above. If desired, the effective daily dose of a therapeutic composition may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical formulation (composition).

Therapeutic compositions can be administered with medical devices known in the art. Examples of well-known implants, delivery systems, and modules useful in the present invention are known to those skilled in the art.

The following examples are intended to illustrate, rather than limit, the invention Example 1

Discovery of a Specific Site for Carbamylation of Human Serum Albumin

To map potential sites on circulating albumin susceptible to carbamylation, we reacted purified human serum albumin (HSA) with potassium cyanate (1 mM) in a physiologic buffer and digested with trypsin or endoproteinase Glu-C. Using reverse phase liquid chromatography and tandem mass spectrometry (product ion scan), we detected one predominant site with appreciable carbamylation at lysine 549. Peptide identification and localization of the carbamylated lysine were obtained by MS/MS ion search using the Mascot search engine, and confirmed by manual reconstruction from MS/MS spectra (FIGS. 3A-3D). When we tested serum albumin from patient samples, lysine 549 was the only detectable site of carbamylation. This finding was consistent with a recent report demonstrating that lysine 549 is most frequent site of glycation as well (Frolov et al., *Anal. Bioanal. Chem.* 397:2349-56, 2010). After our original observation of this carbamylation site on human serum albumin, we subsequently found that an independent group had discovered carbamylation modifications on albumin in rats administered cyanate, and that one of these modifications was also found on lysine 549, the site orthologous to the site we found in human albumin (Kassa et al., *Food Chem. Toxicol.* 49:571-8).

The methods employed to identify this site are as follows. Purified human serum albumin from Sigma was dissolved at 4 mg/ml in standard phosphate-buffered saline and mixed with freshly dissolved 1 mM potassium cyanate, the pH of the mixture was confirmed to be 7.4. Albumin was carbamylated overnight at 37° C., then phosphate buffer and excess cyanate were removed by dialyzing against water. 8 mM dithiothreitol and 1 mM EDTA were added and the albumin was reduced and denatured by heat at 80° C. for 20 minutes. Ammonium bicarbonate (pH 7.8) was added to 100 mM final concentration, and aliquots were digested 37° C. overnight with either trypsin or Glu-C endoproteinase, and acidified with formic acid (1% w/v) before LC-MS analysis.

Example 2

Assay Development for Carbamylated Albumin

Figure 4:
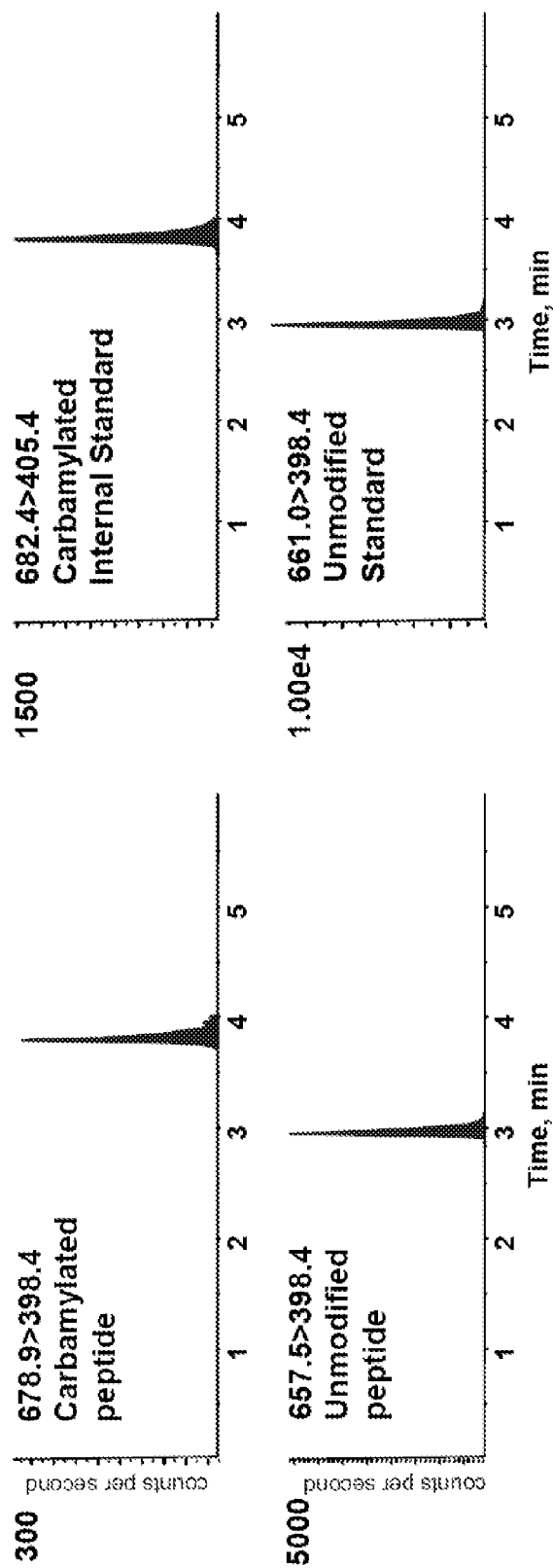
FIG. 4 is a set of graphs showing reverse phase chromatography and multiple reaction monitoring for measurement of % carbamylated albumin in a representative serum sample digested with Glu-C endoprotease. Upper panels show chromatograms for carbamylated peptide forms, both endogenous (left) and isotopic peptide standard (right). Lower panels show non-carbamylated peptide forms, both endogenous (left) and isotopic peptide standards (right). MS/MS mass transitions are shown (e.g. m/z 682.4>405.4 are parent and daughter ions for monitoring for carbamylated isotopic peptide standard).

We next developed methods for LC separation and MS/MS multiple reaction monitoring for our peptides of interest and isotopic peptide internal standards (FIG. 4). In order to apply this assay for the measurement of % C-Alb in patient samples, specimen processing and analysis methods were optimized, and the assay was calibrated by incorporation of isotopic peptide standards in the final method. The final assay method demonstrated excellent linearity (FIG. 5) and precision (coefficient of variation 4.2%). These methods are detailed below.

Carbamylation titration experiments were performed using an amino acid standard mix from Sigma Aldrich (Cat. No. AAS18) supplemented with tryptophan, cysteine, and glutamine; all amino acids were equimolar (2.5 mM stock). The 0.1 N HCl in the standard solution was neutralized with ammonium hydroxide and removed by lyophilization, and the dried amino acids were diluted to final concentration of 50 µM (each) in 100 mM potassium phosphate pH 7.4. 20 mM potassium cyanate (in 100 mM potassium phosphate pH 7.4) was then titrated into the amino acids with final concentrations ranging from 0 to 10 mM, and carbamylation reactions were allowed to proceed overnight at 37° C. Carbamylation was halted with addition of 1 M HCl, and excess cyanate and HCl were removed by vacuum lyophilization at room temperature. Isotopic standards were then mixed with the reactions, the tube were re-lyophilized, and amino acid mixtures were then S-alkylated with iodoacetamide, butylated with butanolic HCl, and analyzed using methods similar to those described for serum amino acids.

To prepare for LC-MS experiments searching for sites of albumin carbamylation, we first calculated the expected m/z values of carbamylated peptides liberated by trypsin or Glu-C digestion, limiting our search for sites of carbamylation to lysine side chains and the amino terminus. Predicted ion masses for potentially carbamylated peptides were calculated using software provided by the Swiss Institute for Bioinformatics on their ExPASy Proteomics Server. We then performed a series of LC-MS/MS scanning experiments screening for digested peptides of the predicted masses. Briefly, 3 µl aliquots of each digest were injected onto a C18 reverse phase column, and peptides were separated using a gradient of 3%-85% acetonitrile in 0.1% formic acid. Each experiment screened for four of the predicted peptide ions, and these ions were selected for collision-induced dissociation and daughter fragment scanning MS/MS spectra from precursor ions of the expected masses were then submitted for peptide identification to the Mascot public search engine, available from Matrix Science Inc. (Boston, Mass.) at www.matrixscience.com. Search criteria specified the enzyme used for digestion (trypsin or glutamyl endoproteinase) and allowed variable modifications of lysine with carbamyl groups. Mascot MS/MS peptide identifications performed on spectra from both trypsin and Glu-C digests found just one unique site of albumin carbamylation on lysine 549, with MOWSE protein identification scores of 43.1 and 35.4 for the trypsin and Glu-C digested peptides encompassing this residue, respectively. In addition to identification of the site of albumin carbamylation by the Mascot search engine, the carbamylated peptide identification was confirmed by visually comparing MS/MS spectra against the predicted a, b, c, x, y, and z-type ions.

Linearity of the assay method was tested by mixing serum with either pure non-carbamylated isotopic peptide standard (0% carbamylation) versus a 5% mixture of carbamylated and non-carbamylated isotopic peptides, followed by a linear dilution of the two samples to obtain known amounts of carbamylation ranging from 0% to 5%. These serum samples were then denatured, digested and analyzed for their % amounts of isotopic carbamylated peptides, using the non-isotopic endogenous peptides as "inverted" internal standards (as described in Lin et al., *Anal. Chem.* 78:5762-7, 2006). Linearity within this range of values is shown in FIG. 5. The precision of this assay was demonstrated with replicate measurements (n=8) of a random serum sample with 1.4% carbamylated albumin, which demonstrated a standard deviation of 0.06% (CV=4.2%).

Example 3

Serum Measurements of Carbamylated Albumin

After searching for candidate carbamylation sites in cyanate-treated albumin, we sought to test whether these modifications also occurred in vivo. LC-MRM methods described above were optimized to maximize their sensitivity, and then these methods were used to analyze patient serum samples (using serum from patients with uremic kidney disease as well as from healthy controls). Because lysine 549 was also the only detectable site of carbamylation in patient samples, we focused on this site.

To measure carbamylated albumin, serum samples were thawed at room temperature and spun at 14,000 rpm for 10 minutes to remove clots and precipitates. 3 µl of cleared serum was diluted into 100 µl of 8 mM dithiothreitol and 1 mM EDTA and heated to 80° C. for 20 minutes in order to denature and reduce disulfide bonds, then allowed cool. 50 µl aliquots of denatured serum were mixed 1:1 with 200 mM ammonium bicarbonate (pH 7.8) and isotopic peptide standards (1 µl or 762 pmoles of the 5% carbamylated albumin isotopic peptide standards per reaction). Samples were chilled on ice, 5 µg of glutamyl endoproteinase (Glu-C) was added, and mixtures were digested at 37° C. overnight. Samples were mixed with formic acid after digestion (175 mM final concentration), and were analyzed by LC-MRM.

In order to resolve peptides of interest, 10 µl of serum peptide digests were injected onto a C18 reverse phase column and eluted using a mobile phase of 0.1% formic acid and a 10%-85% acetonitrile gradient at a flow rate of 0.7 ml/min, total run time was 6 minutes (Table 1).

TABLE 1

HPLC settings for chromatographic separation of carbamylated and non-carbamylatecarbamylated albumin peptides (flow rate 0.7 ml/min) and MS settings for MRM monitoring.

| Time (min) | % Acetonitrile | Actions |
|---|---|---|
| 0-3.0 | 10-50 gradient | Flow through diverted to waste until 3.0 min |
| 3.1-3.5 | 50-85 gradient | Non-carbamylated peptides elute at 3.2 min, carbamylated peptides eluate at 3.4 min. |
| 3.6-6.0 | 10 isocratic | Flow redirected to waste (re-equilibration) |

MS Settings: Ion Spray Voltage 2500 V, Source temp 450° C., Curtain Gas 25, GS1 50, GS2 50, Collision Gas 8, DP 45, EP 5, CE 35

The carbamylated and non-carbamylated peptides of interest eluted after 2.4 and 2.75 minutes, respectively. A column switching value was used to divert salts and other contaminants to waste during the other periods of the experiment. The carbamylated peptides (isotopic and endogenous) were measured by monitoring their known MS/MS mass transitions at 682.4>405.5 and 678.9.5>398.4, respectively; likewise, the non-carbamylated isotopic and endogenous peptides were monitored using transitions 661>405.5 and 657.5>398.4 (z=+2 for all peptide ions monitored). MS/MS transitions and mass spectrometer settings were optimized using the isotopic peptide standards; settings are shown in Table 1. Peptide signals were quantified by integrating the area under the curve (AUC) for each MRM channel, and the ratios of carbamlylated/non-carbamylated albumin peptides were calculated for both endogenous albumin and isotopic standards. The 5% carbamylated isotopic standards were then used as calibrators in order to calculate the absolute percentage of endogenous carbamylation using the following equation:

$$\% \text{ C-Alb} = 5\% \times \frac{AUC \text{ Ratio of carbamylated/non-carbamylated endogenous peptides}}{AUC \text{ Ratio of carbamylated/non-carbamylated isotopic peptides}}$$

Isotopic peptide standards were generated as follows. Albumin isotopic peptide standards were synthesized and purified at the Molecular Biology Core Facilities of the Dana Farber Cancer Institute. Both synthetic peptides corresponded to the Glu-C proteolytic peptide fragment of albumin with amino acid sequences RQIK-X-QTALVE, where X=lysine or N-ε-carbamoyl-L-lysine, corresponding to the unmodified and carbamylated peptide forms. Fmoc-protected N-ε-carbamoyl-L-lysine used in synthesis of the carbamylated peptide form was purchased from ChemImpex International, Wood Dale, Ill. Both peptides were isotopically labeled with Fmoc-protected L-isoleucine containing 6 atoms of carbon-13 and one nitrogen-15, and their purity and mass were confirmed by MALDI-TOF mass analysis. After synthesis, isotopic peptides were purified by preparative HPLC and their concentrations estimated by UV absorbance. Stock solutions of both peptides were diluted in water each to final concentration of 1 mg/ml (762 µM and 737 µM, respectively) and were then mixed together to achieve a ratio of 5:95 carbamylatecarbamylated/noncarbamylated peptides (5% carbamylation) for routine use. The 5% carbamylated isotopic peptide mixture was then aliquoted and frozen at −80° C. for long-term use. All future batches of synthetic isotopic standard/calibrator have been and will be standardized against this original peptide mixture to ensure stability and reproducibility of the assay results over time.

Example 4

% C-Alb Outperforms eKt/V as a Predictor of Mortality in Patients Commencing Hemodialysis We analyzed 81 serum specimens collected at baseline (at day 90 following initiation of dialysis) from patients ("cases") who had died during the 12-month follow-up period, as well as 106 control specimens from patients who survived and were matched for end-stage renal disease category, gender, race, and age +/−3.5 years. The clinical characteristics of the cases and controls as well as biochemical analyses performed on their day 90 specimens are presented in Table 2.

with elevated % C-Alb. Cox proportional hazard ratio was estimated for the 12-month risk of death associated with log-transformed % C-Alb results (analyzed as a continuous variable). Univariate and multivariate analyses found sig-

TABLE 2

Characteristics of study population by mortality.

|  | All (n = 187) | Surviving Controls (n = 106) | Cases (n = 81) | P-value |
|---|---|---|---|---|
| Age | 69.7 ± 12.7 | 69.5 ± 12.7 | 70.1 ± 12.7 | 0.8062 |
| Male | 51.3% (96) | 51.9% (55) | 50.6% (41) | 0.8634 |
| Race |  |  |  | 0.4617 |
| White | 69.5% (130) | 68.9% (73) | 70.4% (57) |  |
| Black | 29.4% (55) | 29.3% (31) | 29.6% (24) |  |
| Other | 1.1% (2) | 1.9% (2) | 0.0% (0) |  |
| Cause of ESRD |  |  |  | 0.9237 |
| Diabetes | 45.5% (85) | 47.2% (50) | 43.2% (35) |  |
| Hypertension | 40.6% (76) | 38.7% (41) | 43.2% (35) |  |
| Nephropathy | 5.9% (11) | 5.7% (6) | 6.2% (5) |  |
| Other | 8.0% (15) | 8.5% (9) | 7.4% (6) |  |
| Facility Statistic | 1.0 ± 0.4 | 1.0 ± 0.4 | 1.1 ± 0.4 | 0.0792 |
| Systolic Blood Pressure (mmHg) | 146.1 ± 22.7 | 151.2 ± 20.3 | 139.4 ± 24.1 | 0.0005 |
| Diastolic Blood Pressure (mmHg) | 72.7 ± 12.1 | 75.2 ± 10.9 | 69.4 ± 12.9 | 0.0006 |
| Body Mass Index | 26.5 ± 7.0 | 26.5 ± 7.2 | 26.5 ± 7.0 | 0.8991 |
| Alkaline Phosphatase | 101.2 ± 45.4 | 96.1 ± 37.3 | 107.7 ± 53.7 | 0.3136 |
| Albumin | 3.5 ± 0.4 | 3.6 ± 0.4 | 3.4 ± 0.5 | 0.0022 |
| Hemoglobin | 11.9 ± 1.4 | 12.2 ± 1.4 | 11.5 ± 1.5 | 0.0007 |
| Transferrin Saturation | 22.8 ± 8.8 | 24.0 ± 7.8 | 21.2 ± 9.8 | 0.0009 |
| Calcium | 8.8 ± 0.6 | 8.9 ± 0.7 | 8.8 ± 0.6 | 0.3596 |
| Ferritin | 411.5 ± 558.3 | 340.2 ± 305.8 | 508.1 ± 772.4 | 0.3551 |
| Potassium | 4.5 ± 0.7 | 4.4 ± 0.6 | 4.5 ± 0.7 | 0.3896 |
| Phosphorus | 5.0 ± 1.4 | 5.1 ± 1.4 | 5.0 ± 1.3 | 0.4467 |
| Platelets | 250.3 ± 91.9 | 239.7 ± 70.4 | 262.8 ± 111.6 | 0.6005 |
| Intact Parathyroid Hormone | 188.9 ± 186.7 | 198.0 ± 215.4 | 176.3 ± 137.9 | 0.6707 |
| White Blood Cells | 7.6 ± 2.3 | 7.4 ± 2.3 | 8.0 ± 2.4 | 0.0588 |
| Equilibrated Kt/V | 1.3 ± 0.3 | 1.3 ± 0.3 | 1.3 ± 0.3 | 0.3118 |
| Average Blood Urea Nitrogen | 47.8 ± 14.7 | 47.4 ± 14.1 | 48.2 ± 15.6 | 0.7211 |

Laboratory values are for values recorded between 15-90 days after start of dialysis
ESRD = End-stage renal disease
CAD/MI = Coronary artery disease/myocardial infarction
COPD = Chronic obstructive pulmonary disease
PVD = Peripheral vascular disease These specimens were analyzed for levels of % C-Alb as described herein. The fraction of serum albumin that was carbamylated in hemodialysis subjects was significantly increased when compared to control subjects with normal kidney function (0.87% vs. 0.42%, p<0.0001; FIG. 6, left panel). This finding demonstrated the association between chronic uremia and carbamylated albumin levels, providing the first proof-of-principal clinical evidence in support of our assay. Hemodialysis subjects who died during study follow-up had significantly higher average % C-Alb levels on day 90 of the study run-in period compared to subjects who survived (1.01% vs. 0.77%, p=0.0009, FIG. 6, right panel). Although the individuals who died demonstrated significantly higher % C-Alb levels, they did not display any significant increase in their average blood urea nitrogen levels compared to surviving controls (47.2 vs. 48.4 mg/dL, respectively, p=0.7211), indicating that patients' % C-Alb is determined by more than simply time-averaged blood urea nitrogen levels (Table 2).

The increased average % C-Alb observed in patients who died during follow-up suggested a possible association between % C-Alb and all-cause mortality in patients with chronic kidney disease. We therefore sought to determine whether the subjects' carbamylated albumin levels measured at the outset of the study period were predictive of their risk of all-cause mortality in the ensuing 12-month follow-up period by calculating the hazard ratios associated nificant increases in the 12-month risk of death in subjects with higher % C-Alb values, even after adjusting for serum albumin levels and all other significant risk factors (Tables 3A and 3B, multivariate hazard ratios of 3.23).

TABLE 3A

Hazard ratio estimates for mortality by level of carbamylated albumin in 187 cases and controls matched for age, gender, race, and cause of renal failure.

|  | Univariate | | Multivariable | |
|---|---|---|---|---|
| Variables | HR (95% CI) | p-value | HR (95% CI) | p-value |
| Carbamylated Albumin[1] | 3.76 (2.20-6.43) | <0.0001* | 3.23 (1.74-6.00) | 0.0002* |
| Albumin | 0.43 (0.26-0.71) | 0.001* | 0.58 (0.30-0.93) | 0.03* |
| Hemoglobin | 0.79 (0.69-0.91) | 0.001* | 0.96 (0.82-1.14) | 0.65 |
| History of Hypertension | 0.42 (0.25-0.71) | 0.001* | 0.42 (0.23-0.74) | 0.003* |
| Systolic Blood Pressure | 0.98 (0.97-0.99) | <0.0001* | 0.99 (0.98-1.00) | 0.05* |
| History of Diabetes Mellitus | 0.69 (0.40, 1.17) | 0.17 | 1.03 (0.55-1.91) | 0.94 |

TABLE 3A-continued

Hazard ratio estimates for mortality by level of carbamylated albumin in 187 cases and controls matched for age, gender, race, and cause of renal failure.

| Variables | Univariate | | Multivariable | |
|---|---|---|---|---|
| | HR (95% CI) | p-value | HR (95% CI) | p-value |
| Equilibrated Kt/V | 0.74 (0.30-1.80) | 0.50 | | |

*Significant at p < 0.05
[1]Variable has been natural log transformed
Laboratory values were recorded between 15-90 days after start of dialysis

TABLE 3B

Hazard ratio estimates for mortality by tertile of carbamylated albumin.

| | Univariate | | Multivariate | |
|---|---|---|---|---|
| | HR (95% CI) | P-value | HR (95% CI) | P-value |
| Carbamylated Albumin (Upper Tertile)[1] | 2.80 (1.62-4.83) | 0.0002* | 3.16 (1.71-5.84) | 0.0002* |
| Carbamylated Albumin (Middle Tertile)[1] | 1.33 (0.73-2.41) | 0.3473 | 1.49 (0.76-2.91) | 0.2424 |
| BMI | 0.99 (0.96-1.02) | 0.6369 | 1.01 (0.98-1.05) | 0.4259 |
| Albumin | 0.43 (0.26-0.71) | 0.0009* | 0.46 (0.24-0.87) | 0.0161* |
| Calcium | 0.83 (0.60-1.16) | 0.2716 | 1.11 (0.73-1.71) | 0.6248 |
| Phosphorus | 0.90 (0.76-1.06) | 0.2056 | 0.96 (0.79-1.17) | 0.6625 |
| Intact Parathyroid Hormone | 1.00 (1.00-1.00) | 0.3779 | 1.00 (1.00-1.00) | 0.7146 |
| Equilibrated Kt/V | 0.74 (0.30-1.80) | 0.5014 | 0.98 (0.37-2.60) | 0.9710 |
| Systolic Blood Pressure | 0.98 (0.97-0.99) | <0.0001* | | |
| Ferritin | 1.00 (1.00-1.00) | 0.1424 | | |
| Congestive Heart Failure | 1.24 (0.75-2.06) | 0.4026 | | |

*Significant at P < 0.05
[1]Reference group is lower tertile of carbamylated albumin.
Laboratory values are for values recorded between 15-90 days after start of dialysis Additional patient characteristics were included in this analysis but demonstrated no statistically significant risk in univariate analysis. These variables included body mass index, leukocyte count, platelet count, serum concentrations of potassium, phosphorus, calcium, ferritin, alkaline phosphatase, parathyroid hormone, history of coronary artery disease/myocardial infarction, chronic obstructive pulmonary disease, cancer, dyslipidemia, anemia, peripheral vascular disease, cerebrovascular accident, congestive heart failure, atrial fibrillation, and liver disease.

In comparison, HR analysis of other biomarkers often altered in patients with kidney disease (eKt/V, PTH, calcium, hemoglobin) demonstrated no measurable contributions to risk.

To corroborate the major findings from our case-control study cohort, we obtained similarly collected baseline specimens from 1,161 ESRD subjects who had participated in a multicenter randomized controlled clinical trial of hemodialysis patients (RCT cohort), and measured their % C-Alb values (baseline characteristics in Table 4). Univariate and multivariate HR analysis of log-transformed % C-Alb again found significant risk of death among subjects with elevated % C-Alb (Table 5), with HR estimates remarkably close to those observed in the ArMORR study. In this cohort, there was no statistically significant risk associated with subjects' concentrations of serum albumin, blood hemoglobin, or urea reduction ratios.

TABLE 4

Characteristics of RCT study population by mortality.

| | All (n = 1161) | Surviving Controls (n = 1023) | Cases (n = 138) | P-value |
|---|---|---|---|---|
| Age | 66 ± 8 | 65 ± 8 | 68 ± 8 | <0.001 |
| % Male | 53.9 (677) | 53.8 (592) | 54.8 (85) | 0.811 |
| Urea reduction rate | 61.8 ± 11.4 | 61.9 ± 11.3 | 61.5 ± 12.6 | 0.824 |
| Body Mass Index | 27.5 ± 4.8 | 27.7 ± 4.8 | 26.3 ± 4.5 | 0.001 |
| Alkaline Phosphatase | 125 ± 61 | 122 ± 49 | 147 ± 114 | <0.001 |
| Albumin | 3.8 ± 0.3 | 3.83 ± 0.30 | 3.76 ± 0.31 | <0.001 |
| Hemoglobin | 10.9 ± 1.3 | 10.9 ± 1.3 | 10.7 ± 1.4 | 0.018 |

TABLE 4-continued

Characteristics of RCT study population by mortality.

| | All (n = 1161) | Surviving Controls (n = 1023) | Cases (n = 138) | P-value |
|---|---|---|---|---|
| Transferrin Saturation | 22.2 ± 11.3 | 22.5 ± 11.2 | 20.2 ± 11.8 | 0.018 |
| Leukocyte count | 8.1 ± 2.4 | 8.0 ± 2.4 | 8.8 ± 2.8 | <0.001 |
| Co-Morbidities | | | | |
| % CAD/MI | 29.4 (369) | 28.2 (310) | 38.1 (59) | 0.011 |
| % PVD | 44.6 (560) | 42.2 (466) | 60.6 (94) | <0.001 |
| % Congestive Heart Failure | 35.4 (444) | 33.9 (373) | 45.8 (71) | 0.004 |
| % Atrial Fibrillation | 9.3 (117) | 8.2 (90) | 17.4 (27) | <0.001 |

Laboratory values were recorded at baseline (start of the study)
Numbers in parentheses( ) indicate number of subjects in category.
CAD/MI = Coronary artery disease/myocardial infarction
PVD = Peripheral vascular disease Additional patient characteristics were included in this analysis but demonstrated no statistically significant differences between cases and controls. These variables included gender, urea reduction rate, systolic blood pressure, diastolic blood pressure, platelet count, serum concentrations of parathyroid hormone, potassium, calcium, phosphorus, ferritin, LDL cholesterol, and percentage of subjects with histories of diabetes mellitus, hypertension, or cerebrovascular accident.

TABLE 5

RCT study hazard ratio estimates for mortality by level of carbamylated albumin.

| Variables | Univariate | | | Multivariate | | |
|---|---|---|---|---|---|---|
| | HR (95% CI) | | p-value | HR (95% CI) | | p-value |
| Carbamylated Albumin[1] | 3.73 | (2.00-6.96) | <0.001* | 2.64 | (1.36-5.14) | 0.004 |
| Age | 1.04 | (1.02-1.06) | <0.001 | 1.03 | (1.01-1.06) | 0.006 |
| BMI | 0.94 | (0.91-0.97) | 0.001 | 0.96 | (0.92-1.00) | 0.062 |
| Alkaline Phosphatase | 1.004 | (1.002-1.005) | <0.001 | 1.002 | (1.001-1.004) | 0.002 |
| Albumin | 0.50 | (0.30-0.82) | 0.006 | 0.80 | (0.45-1.41) | 0.435 |
| Hemoglobin | 0.87 | (0.77-0.97) | 0.017 | 0.93 | (0.82-1.06) | 0.278 |
| Transferrin Saturation | 0.98 | (0.965-0.996) | 0.016 | 0.99 | (0.97-1.005) | 0.148 |
| Leukocyte count | 1.12 | (1.06-1.19) | <0.001 | 1.09 | (1.03-1.16) | 0.005 |
| CAD | 1.54 | (1.11-2.13) | 0.009 | 1.21 | (0.85-1.74) | 0.291 |
| CHF | 1.61 | (1.18-2.21) | 0.003 | 1.21 | (0.85-1.73) | 0.289 |
| PVD | 2.01 | (1.46-2.78) | <0.001 | 1.65 | (1.16-2.34) | 0.006 |
| Atrial fibrillation | 2.24 | (1.48-3.39) | <0.001 | 1.62 | (0.995-2.64) | 0.053 |
| Urea reduction ratio | 0.998 | (0.973-1.023) | 0.857 | | | |

*Significant at p < 0.05
[1]Variable has been transformed to its natural log.
Laboratory values were recorded at baseline Additional patient characteristics were included in this analysis but demonstrated no statistically significant differences between cases and controls. These variables included gender, systolic and diastolic blood pressure, platelet count, serum concentrations of parathyroid hormone, potassium, calcium, phosphorus, ferritin, LDL cholesterol, and percentage of subjects with histories of diabetes mellitus, hypertension, or cerebrovascular accident.

To simulate its use in a clinical setting, a diagnostic threshold of 1% C-Alb was designated (based upon our preliminary analysis of hazard ratios associated with varying thresholds shown in FIG. 2) to stratify the study population and test its performance as a predictor of risk. Kaplan-Meier analysis of our first case-control cohort demonstrated a striking divergence in the mortality rates between patients with high vs. low baseline % C-Alb values (FIG. 7). This difference was particularly pronounced in the sub-group with eKt/V<1.3. Lastly, we attempted to quantify the clinical significance of carbamylation in subjects who passed away by correlating % C-Alb values with the time elapsed between the day their % C-Alb was measured and their death. Intriguingly, a weak but statistically significant association between increased % C-Alb values and shorter time to death (r=−0.23, p=0.037) was found. By comparison, total serum albumin did not show any significant association (r=0.052, p=0.637).

Other than % C-Alb levels, the only biochemical marker that was significantly associated with mortality in our subjects was serum total albumin. The association between low serum albumin and mortality in patients on hemodialysis has been well described in the literature and is thought to be related to protein-energy wasting in this population. There was concern about possible confounding effects between % C-Alb and total albumin levels due to the inherent association between total albumin and % carbamylated albumin, and as a result both the potential for correlation and interaction were explored. A negative and non-significant correlation was observed between serum and carbamylated albumin (r=−0.09, p=0.20). While univariate Cox regression showed that mortality rates were increased in patients in the upper tertile of % C-Alb (p=0.0002) and lower tertile of total serum albumin (p=0.0009), multivariate analyses including interaction terms showed no significant interaction between the upper and middle tertiles of % C-Alb and total serum albumin levels (p=0.90 and 0.75, respectively). The variance inflation factor for both carbamylated and total serum albumin was below 2 and thus did not indicate the potential for collinearity. Finally and most convincingly, although both % C-Alb and total serum albumin concentrations were associated with mortality in univariate HR analysis of our larger RCT cohort, multivariate adjustment for confounding between variables made the risk associated with low serum albumin statistically insignificant, whereas % C-Alb values maintained their association with risk (Table 5). Together these findings indicate that although both % C-Alb values and serum albumin concentrations are associated with risk of mortality in ESRD patients, they are independent of each other and are likely related to mortality via distinct pathophysiologic mechansms.

Although the average BUN and eKt/V values collected on day 90 were not associated with the risk of death observed in this study, these values did demonstrate the expected associations with % C-Alb levels. % C-Alb correlated well with time-averaged 90-day BUN concentrations (r=0.450, p<0.001) and 90-day eKt/V (r=−0.202, p<0.01). Low eKt/V was not associated with increased risk of mortality when adjusted for other variables, nor did adjustment of % C-Alb for eKt/V significantly alter the association between % C-Alb and mortality. Together these data show that % C-Alb is a stronger predictor of death than the standard measure of dialysis adequacy.

The subjects analyzed for this retrospective study were selected from participants in the Accelerated Mortality on Renal Replacement (ArMORR) study as described in (Gutierrez et al., N. Engl. J. Med. 359:584-92, 2008). The ArMORR study is a prospective cohort study of 10,044 subjects who began hemodialysis treatment at any of the 1056 U.S. dialysis centers operated by Fresenius Medical Care North America (Waltham, Mass.) in 2004 or 2005. All of the subjects underwent 1 year of follow-up except for those who died (15.2%), underwent kidney transplantation (3%), recovered renal function (4%), or transferred to a dialysis unit outside the Fresenius Medical Care North America system before completing 1 year of hemodialysis (12%).

All clinical data were prospectively collected by physicians at the point of care. These data included demographic characteristics of the subjects, coexisting conditions, results of studies performed by a central laboratory (Spectra East, Northvale, N.J.), and outcomes. Plasma and serum samples were obtained at the initiation of outpatient hemodialysis and that would otherwise have been discarded after routine clinical testing were saved and stored in liquid nitrogen. The study was approved by the institutional review board of the Massachusetts General Hospital, which waived the need for informed consent from each patient because all personal identifiers were removed from the blood samples and from the clinical data before transfer to the investigators.

The hemodialysis subjects included in this nested case-control study were derived from a set of ArMORR study subjects who died during the 1-year follow-up period ("cases", n=118) and subjects who survived ("controls", n=236). Cases and controls were matched for race, gender, cause of ESRD, and age +/−3.5 years. In order to estimate the number of cases needed for Kaplan-Meier analysis, for a log-rank test comparing two survival curves with two-sided significance level of 0.05, assuming uniform accrual with follow-up time of 365 days, a sample size of 36 per group is required to obtain a power of at least 0.8 if the two samples have an assumed hazard ratio of 2. 191 specimens from this case-control study were selected based upon the availability of unthawed serum specimens suitable for analysis. Of the 191 subjects selected, 4 were excluded because of insufficient sample for analysis. This selection process provided a total of 81 cases and 106 controls. Serum samples from healthy controls with normal kidney function were obtained from specimens used in a separate study as described in Powe et al. (*J. Bone Miner. Res.* 26:1609-16, 2011).

Example 5

C-Alb and Circulating Free Amino Acids

Based on the fact that each amino acid has at least one available nucleophile for carbamylation, we predicted that patients' free amino acids will inhibit C-Alb formation in vivo just as urea promotes C-Alb formation. To test this, we constructed a model for % C-Alb as a composite function of the balance between serum free amino acid levels and BUN (Table 6).

TABLE 6

Spearman correlations and partial correlations between % C-Alb, blood urea nitrogen, and free amino acids.

| Amino Acids | Unadjusted Correlation | | Partial correlation to A.A., adjusted for BUN | | Partial correlation to BUN, adjusted for A.A. | |
|---|---|---|---|---|---|---|
| | $r_s$ | P-value | Partial $r_s$ | P-value | Partial $r_s$ | P-value |
| Average BUN | 0.431 | <0.0001* | | | | |
| Arginine | −0.357 | 0.0004* | −0.451 | <0.0001* | 0.507 | <0.0001* |
| Lysine | −0.310 | 0.0022* | −0.344 | 0.0007* | 0.454 | <0.0001* |
| Histidine | −0.270 | 0.0082* | −0.346 | 0.0006* | 0.477 | <0.0001* |
| Alanine | −0.341 | 0.0007* | −0.345 | 0.0007* | 0.434 | <0.0001* |
| Glycine | −0.216 | 0.0354* | −0.149 | 0.1513 | 0.406 | <0.0001* |
| Threonine | −0.105 | 0.3121 | −0.096 | 0.3556 | 0.430 | <0.0001* |
| Serine | −0.270 | 0.0081* | −0.326 | 0.0014* | 0.464 | <0.0001* |
| Proline | −0.174 | 0.0914 | −0.229 | 0.0261* | 0.425 | <0.0001* |
| Glutamine | −0.238 | 0.0204* | −0.319 | 0.0017* | 0.474 | <0.0001* |
| Methionine | −0.094 | 0.3672 | −0.024 | 0.8220 | 0.423 | <0.0001* |
| Tyrosine | −0.080 | 0.4384 | −0.093 | 0.3725 | 0.433 | <0.0001* |
| Valine | −0.240 | 0.0193* | −0.343 | 0.0007* | 0.488 | <0.0001* |
| Leucine/Isoleu | −0.388 | 0.0001* | −0.448 | <0.0001* | 0.484 | <0.0001* |
| Aspartic Acid | −0.218 | 0.0338* | −0.258 | 0.0121* | 0.450 | <0.0001* |
| Glutamic Acid | −0.060 | 0.5629 | −0.037 | 0.7239 | 0.429 | <0.0001* |
| Phenylalanine | −0.134 | 0.1939 | −0.215 | 0.0373* | 0.458 | <0.0001* |
| Tryptophan | −0.100 | 0.3352 | 0.039 | 0.7099 | 0.423 | <0.0001* |
| Cystine | 0.300 | 0.0036* | 0.255 | 0.0137* | | |

All Spearman rank correlation coefficients and P-values reflect associations with carbamylated albumin.
Left columns: Unadjusted spearman rank correlations compared to % C-Alb.
Middle columns: Partial spearman correlations between amino acid levels and % C-Alb after adjustment for average pre-dialysis BUN values recorded between 15-90 days after start of dialysis.
Right columns: Partial spearman correlations between average pre-dialysis BUN values and % C-Alb after adjustment for amino acid levels measured on day 90.
*Significant at P < 0.05

Each subject's time-averaged urea concentration was estimated by calculating their average pre-dialysis BUN during days 15-90 of the study run-in period. As expected, there was a modest but statistically significant correlation between average BUN and day 90% C-Alb levels (Table 6, top row left, r=+0.431, p<0.0001). In contrast, individual serum free amino acid levels were generally negatively correlated with % C-Alb (Table 6, left columns). Furthermore, when the partial correlation coefficients for each amino acid after adjusting for average BUN were calculated, the strength of these correlations increased (middle columns). When the partial correlation coefficients between average BUN and % C-Alb were calculated, adjusting for individual amino acid levels also generally strengthened the association between % C-Alb and average BUN (right columns). Next, when subjects were stratified by their amino acid levels, we observed proportional differences in % C-Alb, suggesting a "dose-response" relationship between amino acid levels and protein carbamylation. For example, subjects with low vs. high arginine levels had median % C-Alb of 0.90% and 0.68%, respectively (p<0.05, see Table 7).

TABLE 7

Comparison of median carbamylated albumin by amino acids tertile.

| Amino Acids | Tertile 1 | Tertile 2 | Tertile 3 |
|---|---|---|---|
| Arginine | 0.0090[a] | 0.0086[b] | 0.0068[a,b] |
| Lysine | 0.0085[a] | 0.0085[b] | 0.0067[a,b] |
| Histidine | 0.0085 | 0.0084 | 0.0074 |
| Alanine | 0.0087[a] | 0.0082 | 0.0070[a] |
| Glycine | 0.0089 | 0.0081 | 0.0076 |
| Threonine | 0.0080 | 0.0087 | 0.0076 |
| Serine | 0.0092[a] | 0.0084 | 0.0074[a] |
| Proline | 0.0085 | 0.0079 | 0.0077 |
| Glutamine | 0.0089 | 0.0078 | 0.0078 |
| Methionine | 0.0085 | 0.0074 | 0.0077 |
| Tyrosine | 0.0082 | 0.0085 | 0.0077 |
| Valine | 0.0085[a] | 0.0085 | 0.0066[a] |
| Leucine | 0.0090[a] | 0.0086[b] | 0.0066[a,b] |
| Aspartic Acid | 0.0090 | 0.0078 | 0.0081 |
| Glutamic Acid | 0.0082 | 0.0078 | 0.0084 |
| Phenylalanine | 0.0085 | 0.0084 | 0.0075 |
| Tryptophan | 0.0080 | 0.0084 | 0.0081 |

Finally, despite the shorter half-life of serum free amino acids compared to albumin, the percentage of carbamylated free amino acids also correlated well with % C-Alb (Table 8).

TABLE 8

Correlations between carbamylated amino acids ratio (carbamylated amino acids/total amino acids) and carbamylated albumin.

| Carbamylated Amino Acid Ratio | $r_s$ | p-value | Partial $r_s$ | Partial p-value |
|---|---|---|---|---|
| Arginine | 0.149 | 0.1482 | 0.156 | 0.1365 |
| Lysine | 0.481 | <0.0001* | 0.450 | <0.0001* |
| Histidine | 0.567 | <0.0001* | 0.534 | <0.0001* |
| Alanine | 0.295 | 0.0037* | 0.284 | 0.0059* |
| Glycine | 0.292 | 0.0041* | 0.296 | 0.0040* |
| Threonine | 0.229 | 0.0255* | 0.215 | 0.0381* |
| Serine | 0.418 | <0.0001* | 0.408 | <0.0001* |
| Proline | 0.276 | 0.0067* | 0.262 | 0.0110* |
| Glutamine | 0.457 | <0.0001* | 0.426 | <0.0001* |
| Methionine | 0.246 | 0.0163* | 0.218 | 0.0362* |
| Tyrosine | 0.370 | 0.0002* | 0.339 | 0.0009* |
| Valine | 0.667 | <0.0001* | 0.663 | <0.0001* |
| Cystine | 0.027 | 0.7916 | 0.017 | 0.8719 |
| Leucine | 0.414 | <0.0001* | 0.401 | <0.0001* |
| Aspartic Acid | 0.124 | 0.2310 | 0.078 | 0.4571 |
| Glutamic Acid | 0.397 | <0.0001* | 0.355 | 0.0005* |
| Phenylalanine | 0.396 | <0.0001* | 0.394 | <0.0001* |

All Spearman rank correlation coefficients and p-values reflect associations with carbamylated albumin.
Partial spearman correlations are adjusted for congestive heart failure and equilibrated Kt/V at 15-90 days or 91-180 days after the start of dialysis where earlier samples are not available.
*Significant at p < 0.05

Together, these amino acid studies supported our hypothesis that both free amino acids and serum proteins represent two species vulnerable to carbamylation by urea-derived isocyanate and were consistent with our model that both increased urea and decreased amino acid concentrations make additive and independent contributions to protein carbamylation.

Measurement of amino acids concentrations in these experiments were performed as follows. Amino acid analysis methods were adapted from (Dietzen et al., Methods. Mol. Biol. 603:27-36, 2010; Suh et al., J. Chromatogr. B Analyt. Technol. Biomed. Life Sci. 877:3418-27, 2009). Briefly, 20 µl of serum was mixed with 10 µl of isotopic amino acids standards diluted in water and 10 µl of 15 mM iodoacetamide (each reaction containing 2 µl of isotopic amino acid internal standard stock solutions described above). Serum free thiols were allowed to alkylate in the dark for 2 hours at room temperature. Serum proteins were then precipitated by mixing with 120 µl acetonitrile (75% final concentration), and precipitates were cleared by centrifuging at 14,000 rpm for 10 minutes. 100 µl of supernatant was transferred into a new tube and SpeedVac lyophilized. Dried extracts were then derivatized by suspending the pellets in 50 µl of 3M butanolic HCl and heating to 60° C. for 15 minutes (a protocol that minimized in vitro deamidation of glutamine). Butanolic HCl was removed by vacuum drying at room temperature, and the butylated extracts were dissolved in 20 µl water for analysis. Analysis was performed by reverse phase chromatography on a C18 column using a mobile phase of 0.1% formic acid and 3%-50% gradient of acetonitrile. Additional LC settings are shown in Table 9.

TABLE 9

HPLC settings for chromatographic separation of carbamylated and non-carbamylated amino acids (flow rate 0.8 ml/min).

| Time (min) | % Acetonitrile | Actions |
|---|---|---|
| 0-1.0 | 3 isocratic | Flow diverted to waste until 1.1 min |
| 1.0-5.0 | 3-50 gradient | |
| 6.0-6.5 | 50 isocratic | |
| 6.6-10.0 | 3 isocratic | Diverted to waste at 9.0 min (re-equilibration) |

MS/MS transitions and settings for each of the amino acids and their carbamylated forms are shown in Table 10.

TABLE 10

MRM mass spectrometer settings.

| Amino Acid | DP | CE | RT | Endogenous Parent | Daughter | IS Parent | Daughter |
|---|---|---|---|---|---|---|---|
| Ala | 30 | 12 | 3.3 | 146 | 44 | 150 | 47 |
| cAla | 30 | 30 | 5.5 | 189 | 44 | 193 | 47 |
| Arg | 50 | 25 | 1.7 | 231 | 70 | 241 | 75 |
| cArg | 50 | 15 | 3.6 | 274 | 70 | 284 | 75 |
| Glu | 35 | 25 | 6.4 | 260 | 84 | 266 | 89 |
| cGlu | 40 | 35 | 8.5 | 303 | 84 | 309 | 89 |

TABLE 10-continued

MRM mass spectrometer settings.

| | | | | MRM Transition | | | |
|---|---|---|---|---|---|---|---|
| Amino Acid | DP | CE | RT | Endogenous Parent | Daughter | IS Parent | Daughter |
| Gln | 30 | 17 | 3.3 | 203 | 84 | 210 | 89 |
| cGln | 30 | 25 | 1.6 | 246 | 84 | 253 | 89 |
| Gly | 35 | 10 | 2.4 | 132 | 76 | 135 | 79 |
| cGly | 25 | 20 | 5.1 | 175 | 76 | 178 | 79 |
| His | 35 | 12 | 1.2 | 212 | 110 | 221 | 118 |
| cHis | 30 | 30 | 3.3 | 255 | 110 | 264 | 118 |
| Ile | 35 | 10 | 5.4 | 188 | 86 | 195 | 92 |
| cIle | 35 | 25 | 7.8 | 231 | 86 | 238 | 92 |
| Leu | 35 | 10 | 5.4 | 188 | 86 | 195 | 92 |
| cLeu | 35 | 40 | 7.8 | 231 | 86 | 238 | 92 |
| Lys | 30 | 15 | 1.4 | 203 | 84 | 211 | 90 |
| cLys | 30 | 30 | 3.6 | 246 | 84 | 254 | 90 |
| Met | 35 | 10 | 4.9 | 206 | 104 | 212 | 109 |
| cMet | 35 | 60 | 6.9 | 249 | 61 | 255 | 63 |
| Phe | 35 | 15 | 5.8 | 222 | 120 | 232 | 129 |
| cPhe | 25 | 25 | 8.1 | 265 | 120 | 275 | 129 |
| Pro | 30 | 10 | 3.8 | 172 | 70 | 178 | 75 |
| cPro | 40 | 60 | 6 | 215 | 70 | 221 | 75 |
| Ser | 25 | 20 | 2.6 | 162 | 60 | 166 | 63 |
| cSer | 30 | 30 | 4.2 | 205 | 60 | 209 | 63 |
| Thr | 25 | 20 | 3.2 | 176 | 74 | 181 | 78 |
| cThr | 35 | 25 | 4.7 | 219 | 74 | 224 | 78 |
| Tyr | 35 | 12 | 4.9 | 238 | 136 | 248 | 145 |
| cTyr | 40 | 25 | 6.6 | 281 | 136 | 291 | 145 |
| Val | 35 | 10 | 4.7 | 174 | 72 | 180 | 77 |
| cVal | 25 | 30 | 7 | 217 | 72 | 223 | 77 |
| Trp | 60 | 35 | 6.2 | 261 | 159 | 274 | 171 |
| Cystine | 35 | 30 | 4.2 | 353 | 130 | 361 | 133 |
| carbamyl Cystine | 35 | 15 | 5.9 | 396 | 351 | 404 | 359 |
| dicarbamyl Cystine | 35 | 25 | 8 | 439 | 394 | 447 | 402 |
| Cysteine | 35 | 25 | 2.4 | 235 | 116 | 239 | 119 |
| cCysteinyl | 35 | 25 | 2.9 | 278 | 116 | 282 | 119 |
| Asp | 35 | 25 | 4.9 | 246 | 88 | 251 | 92 |
| cAsp | 35 | 25 | 6.2 | 289 | 88 | 294 | 92 |
| GlycylGly | 35 | 30 | 3.2 | 189 | 76 | N/A | N/A |
| cGlycylGly | 35 | 30 | 4.3 | 232 | 76 | N/A | N/A |

Prefix "c" denotes carbamlylated form, e.g. cGly = carbamylated glycine.
DP = declustering potential,
CE = collision energy,
RT = retention time,
RT = column retention time,
IS = isotopic internal standard
For all MRM experiments: Ion spray potential = 2500 V, Source temperature = 450° C., Curtain Gas = 25, GS1 = 50, GS2 = 50, Collision Gas = 8, Entrance Potential = 5

A representative chromatogram of the amino acids' MRM total ion counts is shown in FIG. 8. Amino acid standards were used as calibrators for unmodified amino acid measurements.

Isotopic amino acid standards were generated as follows. Cell-free amino acid mixtures containing all 20 common L-amino acids universally labeled with $^{13}C$ and $^{15}N$ were purchased from Cambridge Isotope Laboratories (Cambridge, Mass.) for use as isotopic internal standards in our amino acid analysis experiments. A mixture of carbamylated and noncarbamylated forms of the isotopic amino acid standards were generated in the laboratory by incubating isotopic amino acids (4 mg/ml) in 20 mM potassium cyanate and 100 mM KH2PO4 (pH 8.0) overnight at 40° C. Carbamylation was halted by the addition of 1M HCl. At low pH, cyanate reacts with water to form carbon dioxide, and excess unreacted cyanate was removed by submitting the reactants to 3 rounds of dilution in 1M HCl followed by vacuum lyophilization at room temperature. The carbamylated reactants were then mixed 1:1 with uncarbamylated isotopic amino acids in order to ensure both carbamylate- carbamylated and non-carbamylatecarbamylated amino acid forms would be present in abundance.

Example 6

Individual Amino Acids' Susceptibility to Carbamylation

To differentiate the isocyanate-scavenging ability of individual amino acids, we added increasing concentrations of cyanate to an equimolar mixture of all twenty amino acids in a physiological buffer. As expected, increasing concentration of cyanate produced linear increases of all carbamylated amino acids and depletion of their unmodified forms (FIGS. 9A and 9B). From the titration curves, we calculated the cyanate concentration at which 10% unmodified amino acid forms were depleted. Arginine and histidine were prone to carbamylation at low cyanate concentrations, consistent with our findings in patient sera. In contrast, lysine did not avidly bind cyanate, likely because its side chain amino group is protonated at physiological pH (Stark G R, Biochemistry 4:1030-6, 1965). The dipeptide glycylglycine was more strongly carbamylated than glycine or other amino acids. Cysteine was found to by modified in two ways; first by oxidation of its free sulfhydryl to form cystine dimers, second by carbamylation of its free amino group to form N-carbamyl-cysteine, N-carbamyl-cystine, and N,N-dicarbamyl-cystine. Oxidation occurred at even the lowest concentrations of cyanate, suggesting a very high cyanate binding avidity by the free thiol group.

These methods were performed as follows. 20 mM solutions of individual amino acids, glutathione, glycylglycine, cysteamine, and taurine were freshly made in 100 mM potassium phosphate. The pH of each was adjusted to pH 7.4 using HCl. HSA (4 mg/mL) was added to each amino acid solution, and then mixed 1:1 with 0.5 mM potassium cyanate in 100 mM potassium phosphate pH 7.4 (0.25 mM cyanate final concentration). Solutions were carbamylated overnight at 37° C., and excess cyanate was removed by adding 10 mM cysteamine and desalting the albumin twice using Zeba spin columns (Pierce Biotechnology, Rockford, Ill.). Desalted albumin was then denatured and digested for analysis as described above.

Example 7

Prevention of Albumin Carbamylation by Amino Acids and Other Candidate Nucleophiles To test whether albumin carbamylation by cyanate is preventable by the presence of competing nucleophiles, we prepared a reaction mixture of human serum albumin (4 mg/ml), 10 mM each of various amino acids and other candidate nucleophiles including glycylglycine, cysteamine and taurine. To this, we added 0.25 mM cyanate, incubated at 37° C. for 14 hours, and analyzed for % C-Alb thereafter (Table 11).

TABLE 11

Inhibition of carbamylation by 10 mM amino acid scavengers.

| Amino acid | % CarbAlb Average +/− SD | P-value (vs. no amino acid added) | % Decrease compared to no inhibitor |
|---|---|---|---|
| Glycylglycine | 15 ± 1.2% | <0.0001 | 63% |
| Cysteine + Cysteamine | 17 ± 0.9% | <0.0001 | 58% |
| Taurine | 22 ± 1.7% | <0.0001 | 44% |
| Cysteamine | 23 ± 1.0% | <0.0001 | 41% |
| Cysteine | 23 ± 1.9% | <0.0001 | 40% |
| Histidine | 26 ± 1.0% | <0.0001 | 33% |
| Arginine | 27 ± 1.6% | <0.0001 | 32% |
| Glutathione | 29 ± 1.4% | <0.0001 | 26% |
| Lysine | 31 ± 0.9% | 0.0002 | 21% |
| Glycine | 31 ± 1.8% | 0.006 | 20% |
| Glutamine | 32 ± 2.9% | 0.009 | 19% |
| Tryptophan | 32 ± 2.7% | 0.012 | 18% |
| Alanine | 32 ± 1.7% | 0.018 | 18% |
| Valine | 33 ± 1.1% | 0.001 | 16% |
| Proline | 34 ± 1.6% | 0.006 | 13% |
| Leucine | 37 ± 2.2% | 0.035 | 7% |
| Glutamate | 38 ± 1.2% | 0.20 | 3% |
| No amino acid | 41 ± 2.5% | | |
| No cyanate | 1.7 ± 0.2% | | |

Glycylglycine reduced the amount of albumin carbamylation by 63%. Cysteine, cysteamine, and the combination of the two also prevented C-Alb formation. Taurine, the most abundant intracellular amine (Chesney R W, Adv. Pediatr. 32:1-42, 1985), also effectively scavenged cyanate. These results demonstrated that albumin carbamylation can be counteracted by free amino acids.

Example 8

Correlation Between Serum Carbamylated Albumin and Average Blood Urea Nitrogen as Evidence of the Chemical Mechanism of Carbamylation, and the Lack of Correlation to Serum Myeloperoxidase or Thiocyanate Concentrations Reactive isocyanate may be derived from spontaneous dissociation of urea or from the enzymatic action of myeloperoxidase on thiocyanate. It has been shown that urea, cyanate, and thiocyanate are all increased in uremic patients. To investigate the chemical source of reactive isocyanate and cause of serum protein carbamylation in uremic patients, we sought to test whether albumin carbamylation in the serum of the 191 ArMORR study subjects was associated with either average blood urea nitrogen (BUN) concentrations or with serum myeloperoxidase and thiocyanate concentrations.

| | Unadjusted | | Partial correlation to myeloperoxidase or thiocyanate, adjusted for BUN | | Partial correlation to BUN, adjusted for Myeloperoxidase or Thiocyanate | |
|---|---|---|---|---|---|---|
| | Correlation | | Partial | | Partial | |
| Variables | $r_s$ | P-value | Partial $r_s$ | P-value | Partial $r_s$ | P-value |
| Average BUN | 0.431 | <0.0001* | | | | |
| Myeloperoxidase | −0.023 | 0.7628 | 0.066 | 0.3838 | 0.448 | <0.0001* |
| Thiocyanate | −0.054 | 0.4652 | −0.095 | 0.2044 | 0.455 | <0.0001* |

All Spearman rank correlation coefficients and P-values reflect associations with carbamylated albumin.
*Significant at P < 0.05

A strong and statistically significant correlation between serum average BUN concentrations and % C-Alb was demonstrated in these uremic patients. In comparison, no correlation was found with serum myeloperoxidase or thiocyanate concentrations, suggesting that although MPO and thiocyanate might be additional contributors to serum protein carbamylation in uremic states, they are not the predominant source.

Other Embodiments

All patents, patent applications, and publications mentioned in this specification, including U.S. Patent Application Nos. 61/507,298 and 61/551,645, are herein incorporated by reference to the same extent as if each independent patent, patent application, or publication was specifically and individually indicated to be incorporated by reference.

The invention claimed is:

1. A method for diagnosing kidney disease, determining the likelihood of developing kidney disease, or determining the severity of kidney disease in a subject, said method comprising:
   (a) determining the fraction of lysine-carbamylated albumin in a biological sample of said subject by:
      (i) enzymatically digesting serum proteins in the biological sample; and
      (ii) detecting carbamylated albumin that has a carbamylated lysine residue, and
   (b) comparing the fraction of lysine-carbamylated albumin in the biological sample of the subject to a control sample,
   wherein an increased fraction of lysine-carbamylated albumin in the biological sample of the subject relative to the control sample is indicative of the presence of kidney disease, an increased likelihood of developing kidney disease, or an increased kidney disease severity.

2. The method of claim 1, wherein said kidney disease severity is indicative of an increased risk of near-term mortality.

3. The method of claim 2, wherein said increased risk of mortality is determined based on said subject having greater than 1.00% lysine-carbamylated albumin in the biological sample of the subject relative to a control sample.

4. The method of claim 2, wherein said near-term mortality is within one year.

5. The method of claim 1, wherein the carbamylated lysine residue is lysine 549.

6. The method of claim 1, further comprising determining the level of free amino acids in said subject, where a decreased level of free amino acids is indicative of increased disease severity.

7. The method of claim 1, wherein said subject is a human.

8. The method of claim 1, wherein said biological sample is a blood sample or a blood serum sample.

9. The method of claim 1, wherein said determining is performed using mass spectroscopy, or wherein said determining is performed using an antibody or an antigen-binding fragment thereof, or wherein said determining is performed using an enzyme-linked immunosorbent assay (ELISA).

10. The method of claim 9, wherein said antibody or antibody fragment is conjugated to a detectable label.

11. The method of claim 1, wherein said kidney disease is end-stage renal disease.

12. A method comprising determining the fraction of lysine-carbamylated albumin in a biological sample of a subject by:
   (i) enzymatically digesting serum proteins in the biological sample; and
   (ii) detecting carbamylated albumin that has a carbamylated lysine residue,
   wherein said subject has or is suspected of having kidney disease.

13. The method of claim 12, wherein the carbamylated lysine residue is lysine 549.

14. The method of claim 12, wherein said subject is a human.

15. The method of claim 12, wherein said biological sample is a blood sample or a blood serum sample.

16. The method of claim 12, wherein said determining is performed using mass spectroscopy, or wherein said determining is performed using an antibody or an antigen-binding fragment thereof, or wherein said determining is performed using an enzyme-linked immunosorbent assay (ELISA).

17. The method of claim 16, wherein said antibody or antibody fragment is conjugated to a detectable label.

18. The method of claim 12, wherein said kidney disease is end-stage renal disease.

* * * * *